United States Patent
Diller et al.

(10) Patent No.: US 8,672,899 B2
(45) Date of Patent: Mar. 18, 2014

(54) MEDICATION INJECTOR APPARATUS WITH DRIVE ASSEMBLY THAT FACILITATES RESET

(75) Inventors: Mark Gerard Diller, Clayton, OH (US); Peter Andrew Gaydos, Hilliard, OH (US); Shannon Marie-Lynn Hoste, Westerville, OH (US); Bobby Lee Walters, Columbus, OH (US); Douglas Edward Boyd, Dublin, OH (US)

(73) Assignee: Eli Lilly and Company, Indianapolis, IN (US)

( * ) Notice: Subject to any disclaimer, the term of this patent is extended or adjusted under 35 U.S.C. 154(b) by 916 days.

(21) Appl. No.: 12/652,837

(22) Filed: Jan. 6, 2010

(65) Prior Publication Data
US 2010/0106098 A1  Apr. 29, 2010

Related U.S. Application Data

(62) Division of application No. 11/669,186, filed on Jan. 31, 2007, now Pat. No. 7,704,238, which is a division of application No. 10/477,781, filed as application No. PCT/US02/11876 on May 8, 2002, now Pat. No. 7,195,616.

(60) Provisional application No. 60/291,437, filed on May 16, 2001, provisional application No. 60/297,051, filed on Jun. 8, 2001, provisional application No. 60/303,613, filed on Jul. 6, 2001, provisional application No. 60/324,199, filed on Sep. 21, 2001.

(51) Int. Cl.
*A61M 5/315* (2006.01)
*A61M 5/00* (2006.01)

(52) U.S. Cl.
USPC .................................. 604/218; 604/207

(58) Field of Classification Search
USPC ................. 604/207–211, 218, 221, 224
See application file for complete search history.

(56) References Cited

U.S. PATENT DOCUMENTS

| 4,315,252 A | * | 2/1982 | Tagami | ............................. 341/1 |
| 4,529,401 A | | 7/1985 | Leslie et al. | |
| 4,592,745 A | | 6/1986 | Rex et al. | |
| 4,865,591 A | | 9/1989 | Sams | |

(Continued)

FOREIGN PATENT DOCUMENTS

| EP | 0338806 | 10/1989 |
| EP | 0498737 | 8/1992 |

(Continued)

OTHER PUBLICATIONS

Eli Lilly and Company, Technical Dossier for the HumaPen® Pen-Injector Family, Aug. 15, 2000, pp. 1 and 10-25 provided.

(Continued)

*Primary Examiner* — Kevin C Sirmons
*Assistant Examiner* — Andrew Gilbert
(74) *Attorney, Agent, or Firm* — Edward J. Prein

(57) ABSTRACT

A medication injector apparatus such as an injection pen. The injection pen may include a doseable quantity identifier that uses a rotational matrix and a sensor for electrically sensing the arrangement of the dose setting mechanism of the the pen, which identifier may be part of a therapeutic dose indicating system that utilizes a cartridge recognizer to recognize a concentration of medication so as to allow an automatic determination of a therapeutic dose.

3 Claims, 24 Drawing Sheets

(56) References Cited

U.S. PATENT DOCUMENTS

| | | | |
|---|---|---|---|
| 4,883,472 A | | 11/1989 | Michel |
| 5,279,586 A | | 1/1994 | Balkwill |
| 5,418,362 A | * | 5/1995 | Lusby et al. ............. 250/231.18 |
| 5,509,905 A | * | 4/1996 | Michel .......................... 604/207 |
| 5,626,566 A | | 5/1997 | Petersen et al. |
| 5,628,309 A | | 5/1997 | Brown |
| 5,674,204 A | | 10/1997 | Chanoch |
| 5,688,251 A | | 11/1997 | Chanoch |
| 5,691,646 A | * | 11/1997 | Sasaki .......................... 324/662 |
| 5,704,922 A | * | 1/1998 | Brown .......................... 604/207 |
| 5,728,074 A | * | 3/1998 | Castellano et al. ........... 604/207 |
| 5,743,889 A | | 4/1998 | Sams |
| 5,820,602 A | | 10/1998 | Kovelman et al. |
| 5,920,198 A | * | 7/1999 | Suzuki et al. ................. 324/662 |
| 5,938,642 A | | 8/1999 | Burroughs et al. |
| 5,954,700 A | | 9/1999 | Kovelman |
| 5,957,896 A | | 9/1999 | Bendek et al. |
| 5,961,496 A | | 10/1999 | Nielsen et al. |
| 6,001,089 A | | 12/1999 | Burroughs et al. |
| 6,068,615 A | * | 5/2000 | Brown et al. ................. 604/207 |
| 6,080,090 A | | 6/2000 | Taylor et al. |
| 6,110,152 A | | 8/2000 | Kovelman |
| 6,221,046 B1 | | 4/2001 | Burroughs et al. |
| 6,221,053 B1 | | 4/2001 | Walters et al. |
| 6,235,004 B1 | | 5/2001 | Steenfeldt-Jensen et al. |
| 6,277,099 B1 | | 8/2001 | Strowe et al. |
| 6,340,357 B1 | | 1/2002 | Poulsen et al. |
| 6,482,185 B1 | * | 11/2002 | Hartmann .................... 604/189 |
| 6,585,698 B1 | * | 7/2003 | Packman et al. ............. 604/207 |
| 6,663,602 B2 | | 12/2003 | Moller |
| 7,138,806 B2 | * | 11/2006 | Gafner et al. ................. 324/660 |
| 8,049,519 B2 | * | 11/2011 | Nielsen et al. ................ 324/662 |
| 8,197,449 B2 | * | 6/2012 | Nielsen et al. ................ 604/189 |
| 2002/0020654 A1 | * | 2/2002 | Eilersen ........................ 206/570 |
| 2002/0177923 A1 | | 11/2002 | Steffen |
| 2003/0006209 A1 | | 1/2003 | Stefen et al. |
| 2005/0182360 A1 | * | 8/2005 | Yeandel et al. ............. 604/96.01 |

FOREIGN PATENT DOCUMENTS

| | | |
|---|---|---|
| EP | 0581925 | 2/1994 |
| EP | 0615762 | 9/1994 |
| EP | 0778034 | 6/1997 |
| EP | 0937471 | 8/1999 |
| EP | 0937472 | 8/1999 |
| EP | 1043037 | 10/2000 |
| EP | 1074273 | 2/2001 |
| EP | 1095668 | 5/2001 |
| GB | 2309801 | 8/1997 |
| WO | WO9009202 | 8/1990 |
| WO | WO0041754 | 7/2000 |
| WO | WO0077472 | 12/2000 |
| WO | WO0110484 | 2/2001 |
| WO | WO0156635 | 8/2001 |
| WO | WO02064196 | 8/2002 |
| WO | WO03009461 | 1/2003 |

OTHER PUBLICATIONS

Extended European Search Report from Application No. EP10010749 dated Sep. 16, 2011, including the search opinion, consisting of 13 pages in total.

* cited by examiner

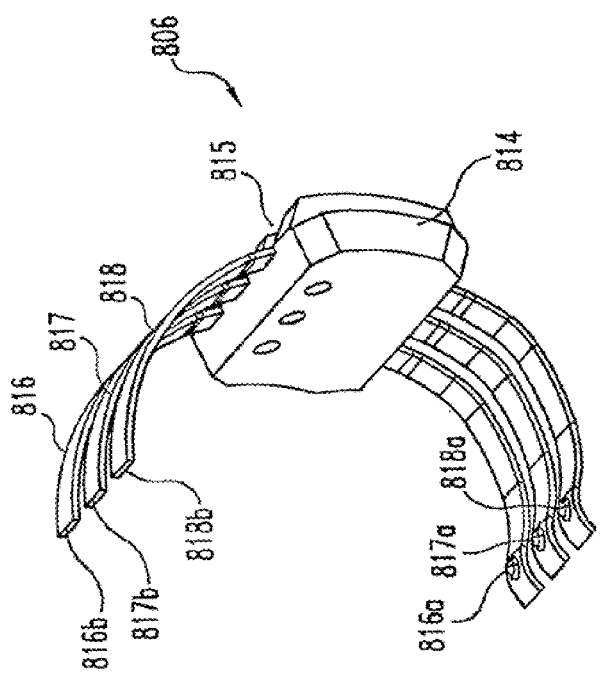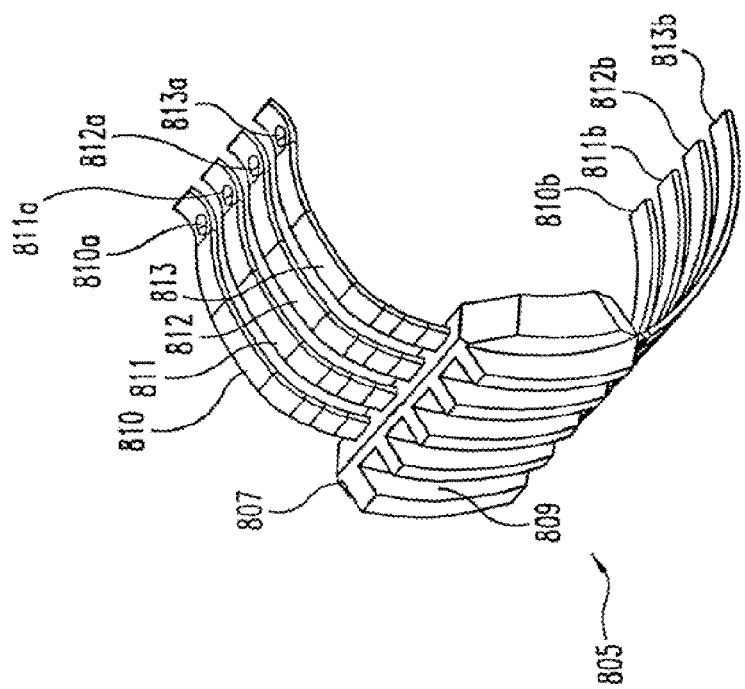
Fig. 29

MEDICATION INJECTOR APPARATUS WITH DRIVE ASSEMBLY THAT FACILITATES RESET

This application is a divisional of Ser. No. 11/669,186 filed Jan. 31, 2007, now U.S. Pat. No. 7,704,238, which was a divisional of Ser. No. 10/477,781 filed May 28, 2004, now U.S. Pat. No. 7,195,616, which was a §371 national application of PCT/US02/l1876 filed May 8, 2002, which claims the benefit of Provisional Application Nos. 60/291,437 filed May 16, 2001; 60/297,051 filed Jun. 8, 2001; 60/303,613 filed Jul. 6, 2001; and 60/324,199 filed Sep. 21, 2001.

BACKGROUND OF THE INVENTION

The present invention pertains to medication delivery devices, and, in particular, to portable medication delivery devices such as injection pens.

Patients suffering from a variety of diseases, such as diabetes, frequently must inject themselves with medication, such as insulin solutions. To permit a person to conveniently and accurately self-administer proper doses of medicine, a variety of devices broadly known as injector pens or injection pens have been developed.

In order to permit a person to administer a proper dose, injection pens have been equipped with a wide variety of dosing and injecting mechanisms that enable a particular dosage to be conveniently selected and then dispensed. Generally, these pens are equipped with a cartridge including a plunger and containing a multi-dose quantity of liquid medication. A drive member is movable forward to advance the plunger in the cartridge in such a manner to dispense the contained medication from the opposite cartridge end, typically through a needle that penetrates a stopper at that opposite end. In reusable pens, after the pen has been utilized to exhaust the supply of medication within the cartridge, a user can remove and dispose of the spent cartridge. Then, to prepare for the next cartridge, the plunger-engaging drive member of the pen is reset to its initial position, either manually or automatically during attachment of a replacement cartridge, and the injection pen can then be used to the exhaustion of that next cartridge.

In order to allow the reset of the plunger-engaging drive member of reusable injection pens, a variety of assemblies have been utilized. One known assembly utilizes a nut fixed within the housing, such as by ultrasonic welding, which nut threadedly engages a drive screw that when rotated is extendable from the base of the injection pen to advance the plunger of a cartridge within a retainer mounted to the pen base. Rotation of the drive screw to screw it through the fixed nut to advance the plunger is effected by a toothed drive clutch, keyed to rotate with the screw, which engages a toothed drive member that rotates during operation of the injecting mechanism. The drive clutch, which is forced into torque transmitting relationship with the drive member when the cartridge retainer is mounted to the pen base, is spring biased away from the toothed drive member when the cartridge retainer is removed. While effective to advance the drive screw, and to allow that screw to be reset or pushed back into the pen base during the process of mounting the cartridge retainer, this assembly is not without its shortcomings. For example, due to the relatively large size of the drive clutch, a flywheel effect of the rotating clutch during screw resetting may cause the screw to retract so far that the initial priming of the pen may be inconvenient to perform.

Injection pens have been equipped with an assortment of mechanisms that generate an audible clicking noise during the injecting process. This clicking noise is intended to inform a user that the pen is operating to administer medication. One known pen uses an injection clicker mechanism which employs a series of radially extending leaf springs arranged around the periphery of a disk-shaped, radially projecting portion of a drive sleeve of the injecting mechanism. As the injecting mechanism of the pen is operated, the drive sleeve rotates, causing rotation of a clutch that has been axially moved during pen assembly so as to be engaged by teeth that axially extend in the distal direction from the drive sleeve radially projecting portion. As the clutch rotates, a drive screw that extends through the drive sleeve and to which the clutch is keyed is caused to rotate, and the drive screw advances axially as it screws through a nut within the pen housing to move a cartridge plunger and expel medicine from the pen. During the drive sleeve rotation, the radially extending leaf springs arranged around the drive sleeve radially projecting portion slip into and out of recesses in the pen housing located radially outward thereof, thereby producing audible clicking noises associated with injection. The leaf springs, when inserted in the housing recesses when drive sleeve rotation is halted, are designed to prevent counter-rotation of the drive sleeve which would allow undesirable back up of the drive screw. While useful, this injection clicker design is not without its shortcomings. For example, modifying the feel and sound of the injection clicks during the design of the pen may involve modifications to the mold cavities of the housing. Still further, the radially extending leaf springs may undesirably increase the overall girth of the injection pen.

In another injection pen disclosed in U.S. Pat. No. 5,688,251, an injection clicker is provided by a spring biased distal clutch with axially facing teeth which is coaxially arranged on and splined to a nut that engages an advanceable lead screw. The spring that pushes the distal clutch teeth against the housing bulkhead to create audible clicking during injection also pushes a proximal clutch against a driver to create audible feedback during dose dialing. While perhaps functional, this design is not without its shortcomings. For example, because the spring used within the injection audible feedback design is also used as part of the dialing audible feedback design, the injection audible feedback cannot be tuned or adjusted by modifying that spring without also affecting the dialing audible feedback, and potentially other features such as dialing torque.

Another limitation of reusable injection pens is that because different types of medicines, provided in separate cartridges, possibly may be utilized with the same reusable pen body, a user of the injection pen and those various cartridges needs to be vigilant to ensure the pen is used to administer the correct dosage of medicine. In order to assist a user in identifying medicine contained in a cartridge, a cartridge recognition system has previously been disclosed in U.S. Pat. No. 5,954,700. In that system, a medicine-filled cartridge includes an information providing source designed to provide information regarding the cartridge to the electronic delivery device, such as an injection pen for which it is adapted. While useful, the information provided does not necessarily result in the delivery device indicating to a user the actual dose of medicine being administered by the delivery device, and calculation errors on the part of the user are possible, resulting in incorrect doses.

Another limitation of some injection pens relates to the dose setting mechanism. One mechanism disclosed in U.S. Pat. No. 5,509,905 includes switches that are used in forming signals when the switches are actuated during rotation by a user of an operating head extending from the pen base. The signals are used in mathematically establishing the number of unit volumes set by the user. However, the use of cams to activate the switches results in the resistance to rotating the operating head noticeably varying during revolution of that operating head.

Another problem with some existing injection pens is that dosing and injecting operations of the pen are not intuitive to all users. In particular, with some pens, the user first must rotate a knob of the pen to set the medicine dose to be delivered as indicated by numbers on a marked dial fixedly connected with the knob, and then must apply an axial or plunging force which moves the knob axially to inject the medicine dose. Because for some pen designs the knob and dial will have axially translated away from the pen base while being rotated during dose setting, and further that knob and dial, when plunged during injecting, will also rotate back into the pen base so as to provide via its markings a continuous indication of the amount of medicine remaining to be delivered, a user may come to believe that rotating down the proximally extended knob will inject the medicine. However, such a belief is erroneous for at least one pen design, and therefore a user who operates under such an erroneous belief may not properly self-administer the desired medicine.

In a well known disposable injection pen design, a dose is similarly set by rotating out a knob, connected to a number-marked dial, such that the dial translates out while rotating. While the dial is rotated, a sequence of numbers helically arranged on the dial is visible through a viewing window to show the dose the pen is then set to deliver. In this design, application of a plunging force moves the knob and the dial axially and without rotation to inject the medicine dose. However, while useful, this design is not without its shortcomings. For one thing, during plunging, few if any of the dose-indicating numbers which have been passed in setting the pen are displayed, which may be a source of confusion for some users. Furthermore, after the pen is used for injecting, the dial has to be reset before it can be screwed outward to set the next dose for delivery. Resetting requires a rotation of the dial to a zero position, except for a limited number of dose quantities previously injected, followed by an axial shifting of the dial.

Thus, it would be desirable to provide a device or method that overcomes one or more of these and other shortcomings of the prior art.

BRIEF SUMMARY OF THE INVENTION

The present invention encompasses a drive assembly that is operable to advance a plunger of a cartridge of a portable injector apparatus such as an injection pen, and which is resettable with minimal effort during replacement of the spent cartridge.

The present invention also encompasses an assembly within a portable injector apparatus that during dose injecting provides to a user an audible indication of operation, which audible indication is readily adjustable by the manufacturer by, for example, a substitution of biasing elements.

The present invention also encompasses a therapeutic dose indicating apparatus for a medicine delivery device, such as an injection pen, which first determines a therapeutic dose based on a sensed medicine concentration and a sensed dose volume setting, and then visibly displays the determined therapeutic dose. The invention further encompasses a doseable quantity identifier for an injection pen which uses a sensor, such as with electrical contacts, to read a matrix to determine how a dose setting mechanism has been rotationally arranged by a user in setting the pen for dose administration.

The present invention also encompasses a medication injector apparatus including an assembly for selectively rotating a drive sleeve, which assembly has a dial that rotates out during dose setting and which translates in without rotation during dose injecting. The dial is keyed to a barrel within the apparatus, and further is threadedly engaged with the drive sleeve that is operably connected to a drive member advanceable to force medication from a fluid container within the apparatus. The relative rotation experienced by the barrel and drive sleeve during dosing and injecting is used by an electrical sensing mechanism in recognizing the arrangement of the apparatus for the purpose of displaying to a user the dose selected and remaining to be injected.

In one form thereof, the present invention provides a resettable, cartridge plunger drive assembly of a dose injecting mechanism of a medication injector apparatus which has a reusable base and a cartridge assembly mountable thereto. The base has a rotatable drive member of the dose injecting mechanism within its housing, and the cartridge assembly has a medicine-filled cartridge with a movable plunger at one end and an outlet at the other end. The drive assembly includes a nut, a screw, a drive clutch, and a biasing element. The nut is keyed to the base housing tube both movable relative thereto between first and second axial positions, and rotatably fixed relative thereto at the first and second axial positions. The screw includes a plunger-engaging distal end and external threading in threaded engagement with an internally threaded opening of the nut. The drive clutch is connected to the nut to be axially retained and rotatably movable relative thereto. The drive clutch is keyed to the screw to be rotatably fixed and axially movable relative thereto. The nut is positioned within the base housing to be axially movable from the first axial position to the second axial position by engagement with the cartridge assembly during mounting of the cartridge assembly to the reusable base. The drive clutch is in torque transmitting engagement with the rotatable drive member when the nut is disposed in the second axial position, whereby rotation of the drive member during operation of the dose injecting mechanism rotates the drive clutch and thereby the screw to produce axial movement of the screw in a distal direction through the nut to thereby advance the plunger-engaging distal end of the screw to force medication from the cartridge outlet. The biasing element biases the nut from the second axial position toward the first axial position when the cartridge assembly is not mounted to the reusable base. The drive clutch is disengaged from torque transmitting engagement with the rotatable drive member when the nut is disposed in the first axial position, whereby application of a force in a proximal direction on the plunger-engaging distal end of the screw axially moves the screw in a proximal direction as it screws through the nut to thereby reset the screw.

In another form thereof, the present invention provides a resettable, cartridge plunger drive assembly of a dose injecting mechanism of a medication injector apparatus which has a reusable base and a cartridge assembly mountable to the base. The apparatus base has a rotatable drive member of the dose injecting mechanism within its housing, and the cartridge assembly has a medicine-filled cartridge with a movable plunger at one end and an outlet at the other end. The drive assembly includes a nut, a screw, a drive clutch, and a biasing element. The nut is keyed to the base housing to be both movable relative thereto between first and second axial positions, and rotatably fixed relative thereto at the first and second axial positions. The screw includes a plunger-engaging distal end and external threading in threaded engagement with an internally threaded opening of the nut. The drive clutch is keyed to the screw to be rotatably fixed and axially movable relative thereto. The nut is positioned within the base housing to be axially movable from the first axial position to the second axial position by engagement with the cartridge assembly during mounting of the cartridge assembly to the reusable base. The drive clutch is structured and arranged to be shifted from a location out of torque transmitting engagement with the rotatable drive member to a location in torque transmitting engagement with the rotatable drive member when the nut is moved from the first axial position to the second axial position, wherein when the drive clutch is in torque transmitting engagement with the rotatable drive member, rotation of the drive member during operation of the dose injecting mechanism rotates the drive clutch and thereby the screw to produce axial movement of the screw in a distal direction through the nut to thereby advance the plunger-engaging distal end of the screw to force medication from the cartridge outlet. The biasing element is structured and arranged to bias the drive clutch from the location in torque transmitting engagement with the rotatable drive member to the location out of torque transmitting engagement with the rotatable drive member, and thereby move the nut from the second axial position toward the first axial position, when the cartridge is not mounted to the reusable apparatus base, wherein when the drive clutch is out of torque transmitting engagement with the rotatable drive member, application of a force in a proximal direction on the plunger-engaging distal end of the screw axially moves the screw in a proximal direction as it screws through the nut to thereby reset the screw.

In another form thereof, the present invention provides an injection clicker assembly of a medication injector apparatus, which apparatus includes a drive screw advanceable in a distal direction to shift a movable plunger of a cartridge so as to force medication from an outlet of the cartridge, a drive sleeve of a dose injecting mechanism rotatable in a first direction within a housing of the apparatus, the drive sleeve including a distal facing surface and defining a longitudinal bore in which the drive screw extends, and a clutch, connected to the drive screw, that is rotated by engagement with the drive sleeve distal facing surface to thereby rotate and advance the drive screw through a nut within the housing. The injection clicker assembly includes a collar arranged coaxially on the drive sleeve at a location proximal of the distal facing surface of the drive sleeve. The collar is connected to the drive sleeve to be axially movable relative thereto and rotatably fixed thereto when the drive sleeve rotates in the first direction. The collar includes a plurality of teeth extending in an axial direction and adapted to engage mating teeth of a stop surface one of integrally formed with and non-rotatably connected to a housing of the apparatus. The injection clicker assembly also includes a biasing element adapted to force the collar axially into meshing engagement with the stop surface. The collar and the stop surface are complementarily configured such that during rotation of the drive sleeve in the first direction, and due to a returning force applied to the collar by the biasing element, the collar oscillates axially on the drive sleeve as the collar teeth slide over the stop surface teeth to provide an audible clicking sound that indicates injecting use of the apparatus.

In another form thereof, the present invention provides a therapeutic dose indicating apparatus for a portable medication injector device which includes an adjustable dose setting mechanism and which is loaded with a replaceable medicine container. The apparatus includes a visible display, a container recognizer that recognizes a concentration of medicine within the container, which container recognizer includes an identifier disposed on the container, a closeable quantity identifier that identifies a volume of medicine selected for delivery by the adjustable dose setting mechanism, and a controller adapted to determine a therapeutic dose based on the recognized concentration and the identified volume and cause the therapeutic dose to be displayed in the visible display.

In another form thereof, the present invention provides a doseable quantity identifier for a medication injector apparatus having a dose setting mechanism operable to select a volume of medicine to be delivered from a held cartridge. The doseable quantity identifier includes a rotational matrix disposed on a first component of the apparatus, a sensor for electrically sensing the rotational matrix, which sensor is disposed on a second component of the apparatus which experiences rotational motion relative to the first component during operation of the dose setting mechanism, whereby data of the rotational matrix sensible by the matrix sensor is thereby indicative of an arrangement of the dose setting mechanism, a controller circuited with the sensor which interprets data of the rotational matrix sensed by the sensor to determine a quantity of medicine to be delivered from the cartridge during injection, and a visible display that displays the quantity of medicine to be delivered as determined by the controller.

In still another form thereof, the present invention provides a method of indicating a therapeutic dose to a user of a portable medication injector apparatus loaded with a cartridge of medicine, the portable medication injector apparatus including a dose setting mechanism operable to select a volume of medicine for delivery. The method includes the steps of recognizing a concentration of the medicine within the cartridge with a cartridge recognizer of the portable medication injector apparatus, identifying a selected delivery volume with a doseable quantity identifier of the portable medication injector apparatus, determining the therapeutic dose with a controller of the portable medication injector apparatus using the recognized concentration and the identified selected delivery volume as input, and displaying the determined therapeutic dose on a display of the portable medication injector apparatus.

In still another form thereof, the present invention provides a medication injector apparatus comprising a housing, a fluid container mounted to the housing defining a medicine-filled reservoir and including a movable piston at a proximal end of the reservoir, a needle assembly removably attached to a distal end of the fluid container to have an injection needle of the needle assembly in flow communication with the reservoir, a drive member advanceable within the housing in a distal direction to move the piston toward the injection needle for forcing medicine from the container, and a dose setting element that includes a control portion external to the housing and manually rotatable in a first direction to screw the dose setting element from a plunged position to a plungeable position at which the dose setting element projects farther proximally from the housing than at the plunged position. The apparatus also includes means, operable by translating without rotation the dose setting element from the plungeable position to the plunged position, for advancing the drive member in the distal direction, the advancing means comprising a drive sleeve and a barrel within the housing that experience relative rotation during at least a portion of a movement of the dose setting element between the plunged position and the plungeable position, and an electronics assembly that displays a dose of medicine to be injected based on a sensing of the relative rotational positions of the barrel and the drive sleeve.

In still another form thereof, the present invention provides a medication injector apparatus including a housing, a medicine-filled container mounted to the housing and including a movable piston at one end and an outlet at the other end, a drive member advanceable within the housing in a distal direction to move the piston toward the outlet for forcing medicine from the container, a drive sleeve around and operatively connected to the drive member, which drive sleeve is rotatable to advance the drive member distally, a barrel around the drive sleeve and movable in the distal direction within the housing by engagement with the drive sleeve from a first axial position to a second axial position, which barrel is freely rotatable relative to the housing at the first axial position and rotatably fixed relative to the housing at the second axial position, a dose setting element including a manually rotatable portion external to the housing, which dose setting element is keyed with the barrel within the housing to be axially movable and rotatably fixed relative to the barrel, and which is in threaded engagement with the drive sleeve. The manually rotatable portion is rotatable in a first direction such that the dose setting element rotates and moves proximally along the drive sleeve due to the threaded engagement therebetween, whereby the dose setting element moves from a plunged position to a plungeable position at which the dose setting element projects farther proximally from the housing than at the plunged position. When the dose setting element is in the plungeable position, application of a force in a distal direction on the dose setting element first translates distally and without rotation the dose setting element and the drive sleeve and the barrel relative to the housing until the barrel shifts from the first axial position to the second axial position, and then, until the dose setting element reaches the plunged position, translates distally and without rotation the dose setting element relative to the housing while thereby rotating without translation the drive sleeve to advance the drive member distally within the housing.

One advantage of the present invention is that a drive assembly can be provided which facilitates reset of an injection pen during installation of a replacement medication cartridge.

Another advantage of the present invention is that a drive assembly can be provided which, without increasing the injection force of the injection pen in which it is used, allows for a biasing element strong enough to force the drive clutch out of engagement with the drive member, thereby avoiding a problem found in the prior art in which a more weakly biased drive clutch could bind to the drive member so as to lock the drive screw and prevent reset.

Another advantage of the present invention is that a drive assembly can be provided which has a relatively small drive clutch to limit flywheel effects during drive screw reset, which in turn may reduce priming volumes.

Another advantage of the present invention is that a drive assembly can be provided which engages a cartridge assembly during its mounting to the pen base so as to reduce play between the cartridge assembly and the pen base, thereby providing an improved fit therebetween and improved quality feel to the injection pen.

Another advantage of the present invention is that a drive assembly with a relatively simple design can be provided to reduce costs of assembly and manufacture.

Another advantage of the present invention is that a drive assembly can be provided which in one embodiment spring biases forward a loaded cartridge to hold it in place against a forward stop of the holder or retainer of the cartridge assembly to ensure a stable platform for dose delivery.

Another advantage of the present invention is that a drive assembly can be provided which in one embodiment is biased together with a loaded cartridge so as to limit relative movement of the cartridge and the drive screw which otherwise could cause drooling of the pen.

Still another advantage of the present invention is that an injection clicker assembly can be provided that generates an audible indication to a user of injecting operation of the portable injector in which it is installed.

Still another advantage of the present invention is that an injection clicker assembly can be provided that is readily tunable during manufacturing design, such as by altering a spring constant or preload of a biasing element, to provide the desired tone and loudness of the injection audible feedback.

Still another advantage of the present invention is that an injection clicker assembly can be provided that can be tuned during manufacture independently of any dialing audible feedback or dialing torque of a pen in which it is installed.

Still another advantage of the present invention is that an injection clicker assembly can be provided that can be designed to serve as an anti-backup mechanism for an advanceable drive screw.

Still another advantage of the present invention is that an injection clicker assembly can be provided that is structured and arranged to utilize space efficiently so as to not adversely impact the length or girth of the pen in which it is installed.

Still another advantage of the present invention is that an injection pen can be provided which electronically displays the dose of therapeutic agent the user has selected for administration by operation of the dose setting mechanism of the pen.

Still another advantage of the present invention is that because the therapeutic dose displayed is a medically important, actual amount of medicine to be administered, rather than a number of clicks or injection pen unit volumes, a user need not make mental calculations regarding dosing which may be subject to error.

Still another advantage of the present invention is that an injection pen can be provided which can be used with various types of medicines while allowing the pen to display dose information related to the particular type, such as strength of concentration, of medicine in use.

Still another advantage of the present invention is that a dose that can be displayed by the injection pen can be determined by the pen after it automatically recognizes the concentration of the contents of a loaded medicine container.

Still another advantage of the present invention is that a rotational matrix that can be used to determine the selected dose volume permits a unique signal for a small, such as fifteen degree, rotational position of the dose setting mechanism, has a compact design to fit within a small physical envelope, and provides a low friction contact solution for dose sensing which does not detract from the ease of operation.

Still another advantage of the present invention is that a rotational matrix can be provided with a feature that enables the microcontroller of the apparatus to determine if an invalid sensed matrix position code should be ignored as an aberration rather than causing the apparatus to immediately display an error message.

Yet another advantage of the present invention is that a medicine injector apparatus can be provided including an assembly for selectively rotating a drive sleeve which has different modes of operation during dose setting and injecting to allow a user to conceptually distinguish between the different stages of apparatus use.

Yet another advantage of the present invention is that a medicine injector apparatus can be provided including an assembly for selectively rotating a drive sleeve which includes a dial that rotates while translating during the dose setting operation, yet which translates without rotating during the dose injecting operation.

Yet another advantage of the present invention is that a medicine injector apparatus can be provided including an assembly for selectively rotating a drive sleeve which during its injecting operation automatically resets the apparatus to a zero position from which its dial can be rotated outward to set the next dose for delivery.

Yet another advantage of the present invention is that a medicine injector apparatus can be provided including a switch within the housing and used in controlling the electronics of the apparatus, such as setting date and time values.

Yet another advantage of the present invention is that the switch that can be provided in the medicine injector apparatus is activated by axial motion of a component within the housing during use, and serves to distinguish between dosing and injecting operations, which among other things makes the switch suitable for triggering a last dose memory function of the pen.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taking in conjunction with the accompanying drawings, wherein:

FIG. 29 is another rear perspective view of the contact assemblies of FIG. 27.

Figure 1:
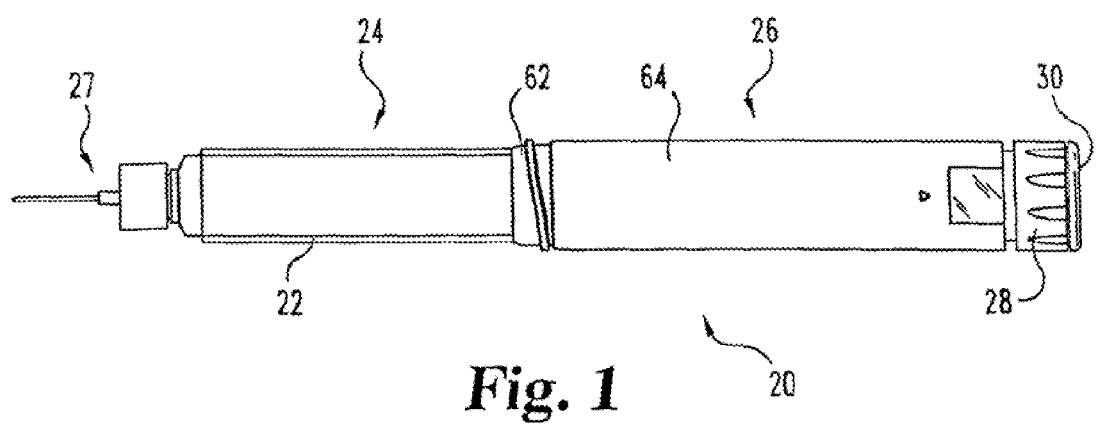
FIG. 1 is a diagrammatic plan view of a medicine injection pen equipped with one form of a dose injecting mechanism including a resettable, cartridge plunger drive assembly of the present invention.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

FIG. 1 generally illustrates one type of medication delivery device in which a drive assembly of the present invention finds beneficial application. The shown delivery device is a reusable, medication injection pen, generally designated 20. As is generally known in reusable devices of its type, injection pen 20 includes a medication filled cartridge 22 as part of a cartridge assembly, generally designated 24, which is connected to a reusable pen base, generally designated 26. Pen base 26 preferably includes dose setting and injecting mechanisms that function to allow a quantity of medicine to be selected and then expelled from cartridge assembly 24 through the injection needle assembly 27 shown attached thereto. In the shown embodiment, an exposed knob 28 with rotatable button 30 thereon at the rearward or proximal end of pen base 26 is a manually operable portion of the dose setting and injecting mechanisms otherwise housed within pen base 26. During the dose setting process, knob 28 is designed to be rotatable to set the dose, and when knob 28 is so rotated to increase the selected dose the knob 28 and button 30 translate out of pen base 26 from the axial position shown in FIG. 1, or to the right from the perspective of a FIG. 1 viewer. During the dose injecting process which occurs after the dose setting process, when a plunging force is applied to button 30, which rotates freely relative to knob 28, button 30 and knob 28 are designed to be shifted to the left, and back to the axial position shown in FIG. 1, to cause the injecting mechanism components housed within the pen base to operate to cause the medicine in the cartridge to be injected.

The foregoing is provided as background and is intended to be illustrative and not limiting in any way, as a variety of injectors, having varied manual dose setting and injecting mechanisms, and having varied external shapes and sizes, are known in the injection pen art. The inventive drive assembly may be readily adapted for many of such mechanisms in view of the explanation herein, as the inventive drive assembly described further below in theory may be incorporated into any type of injecting mechanism that during injection rotates a rotatable drive element that inputs a rotational force to the drive assembly. Additionally, the inventive drive assembly is applicable to autoinjectors having rotatable drive elements, and further does not require the presence of a dose setting mechanism that allows variability in the quantity to be delivered.

Figure 2:
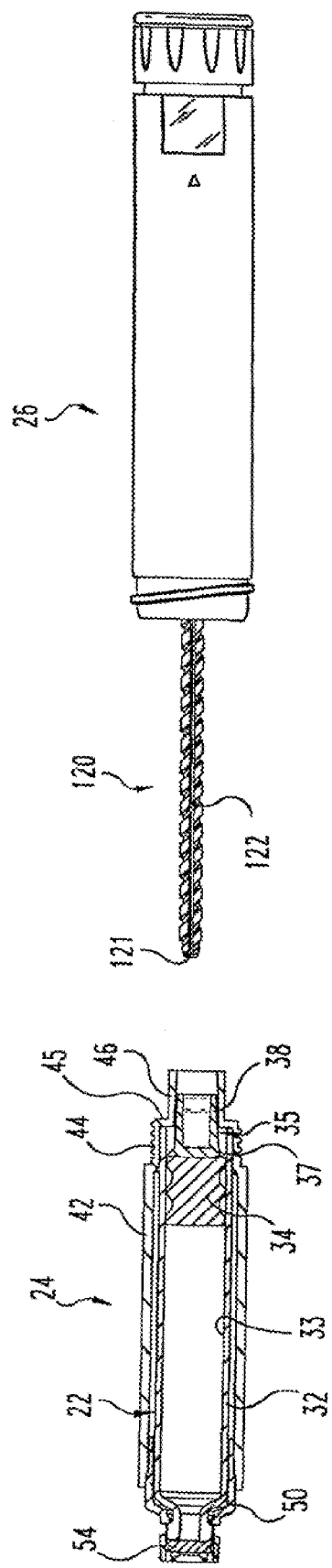
FIG. 2 is a plan view in partial cross-section diagrammatically showing the injection pen of FIG. 1 prior to the mounting of the cartridge assembly to the reusable pen base, and with the drive screw of the drive assembly projecting from the distal end of the pen base.

With additional reference to FIG. 2, in which the needle assembly is not shown attached thereto, cartridge assembly 24 is assembled from component parts during its production into a unit handled by a user as a single piece, and disposed of as a unit when the contained medicine is exhausted. Cartridge 22 of cartridge assembly 24 includes an open-ended glass housing 32 that defines an internal volume filled with medicine such as human growth hormone or insulin. A slidable plunger 34 engages inner surface 33 of the cartridge housing in a fluid-tight manner. A rod tip 35 used to distribute advancing forces applied to plunger 34, and which is freely movable within the cartridge internal volume located proximally of plunger 34, has a base disc 37 integrally formed with a cylindrical collar 38 in which fits the distal end 121 of drive screw 120 of the inventive drive assembly. If rod tip 35 is eliminated, distal end 121 of drive screw 120 can directly, as opposed to indirectly, engage plunger 34. Alternatively when the pen is to be used with cartridges that lack a rod tip, a foot which has a larger diameter than the drive screw and which is designed to rotate relative to the drive screw may be rotatably mounted on distal end 121 to directly engage the cartridge plunger.

Cartridge 22 is further protected by an outer housing 42, which is shown as being transparent but may be otherwise constructed. At its rearward end, outer housing 42 includes an externally threaded, stepped-down neck portion 44, and a further stepped-down rear hub 46 in which extends the rearward end of rod tip 35. Threaded neck portion 44 allows for a threaded or screw attachment of cartridge assembly 24 to pen base 26. Cartridge assembly 24 includes cap 50 that is secured during production, such as by ultrasonic welding, to outer housing 42 to capture cartridge 22 within the outer housing. A pierceable rubber septum 54 is pressed by cap 50 against cartridge housing 32 to seal the open forward end of the housing. External threads on cap 50 allow mounting of injection needle assembly 27. When assembly 27 is so mounted, the rear end of its needle pierces septum 54, and medicine is expressed from cartridge 22 through the needle when plunger 34 is driven to the left in FIG. 1 during injecting use of pen 20.

The cartridge assembly which is acted upon by the drive assembly of the present invention may be differently configured such as is known in the art. For example, and as further shown in FIG. 7, the cartridge assembly may be provided as a reusable retainer which is connectable in suitable fashion, such as via threads, to a reusable pen base, and which retainer defines a chamber into which a disposable cartridge is loaded for use. After the contents of the given cartridge are exhausted by multiple uses of the injection pen, a user disconnects the retainer from the pen base, removes the spent cartridge from the open proximal end of the retainer and disposes of that cartridge, and then inserts a replacement disposable cartridge into the retainer which is then reconnected to the pen base for use, which cartridge replacement process can be repeated as necessary. Still further, other cartridge assemblies may be used, such as a cartridge assembly that includes a disposable cartridge made of plastic and without an outer protective cover, and which attaches directly to the pen base, as well as a cartridge assembly that includes a replaceable cartridge, which mounts or inserts within a chamber of the device, and a cover element for the cartridge-receiving device chamber, such as a separate cap piece or an access door that is slidably or pivotally connected to the device.

With additional reference to FIGS. 3-6, the drive assembly includes a floating nut 60 located within the interior hollow of pen base 26 defined by the pen base exterior housing. In the embodiment diagrammatically shown in FIG. 3, the distal end of the pen base exterior housing includes a cartridge interface member 62 fixedly secured, such as by gluing, plastic snap fit or ultrasonic welding, to a rearwardly extending housing body portion 64. Interface member 62 is internally threaded at 66 for connection to the externally threaded stepped-down neck portion 44 for mounting cartridge assembly 24 to pen base 26. External threading 63 of interface member 62 allows mounting of a not shown main cap of injection pen 20. The inventive drive assembly also may be used with other housing configurations.

Floating nut 60 is molded in one piece from plastic and includes a generally cylindrical, tubular body section 70 which is preferably keyed to the pen base housing to allow the nut to travel in an axial direction therein while preventing rotational motion of the nut within the housing at any given axial position. A suitable keying includes radially projecting keys 74 located adjacent the rearward end of nut body section 70 which fit within axially aligned grooves or keyways 65 formed in housing body portion 64. In the shown embodiment, three equally angularly spaced keys 74 are provided, but additional keys, or fewer keys including only a single key, may be employed. In addition, nut 60 may be keyed to the pen base housing by keys furnished on the housing that fit within keyways formed in the exterior of the nut.

The hollow interior 71 of tubular body section 70 is spanned by disk portion 80 of nut 60. The portion of hollow interior 71 located forward of disk portion 80 is sized to freely rotatably receive hub 46. A central opening 81 defined by disk portion 80 is formed with internal threads 82 designed to mate with external threading 124 of the drive assembly screw 120. A pair of drive clutch retainers 85 are provided on opposite sides of central opening 81. Each drive clutch retainer 85 is a rim or latch portion 87 integrally formed with and projecting radially inwardly from body section 70.

Floating nut 60 is forced toward the forward end of pen base 26 by a biasing element acting between nut 60 and, for example, the pen base housing. One suitable biasing element is a metal, helical compression spring 90 having a forward end 91 that directly abuts the annular end face 72 of body section 70, and a rearward end 92 that directly abuts a protruding bulkhead 93 of housing body portion 64. The rear end surface 67 of interface member 62 provides an axial stop against which the forward face 75 of each nut key 74 abuts to limit forward axial movement of nut 60 by spring 90. Alternate biasing elements, such as different types of springs and different materials of construction, may be substituted in other embodiments. The rearward end of the biasing element alternatively may abut a pen component that is connected to, rather than integrally formed with, the housing.

Figure 3:
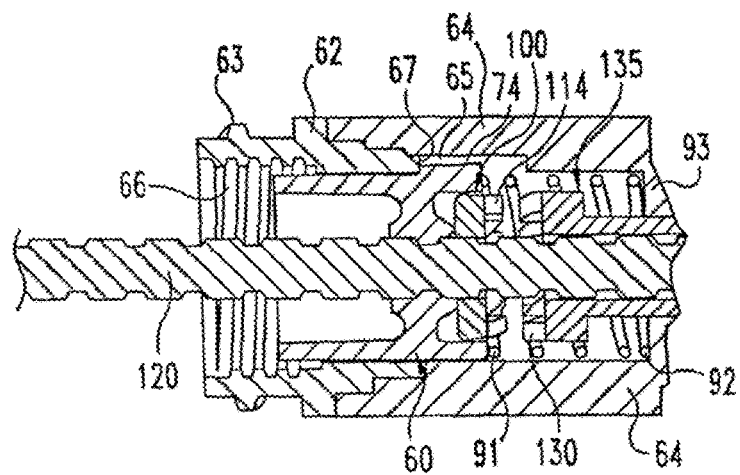
FIG. 3 is a fragmentary plan view in cross-section diagrammatically showing the reusable pen base of FIG. 2.
Figure 6:
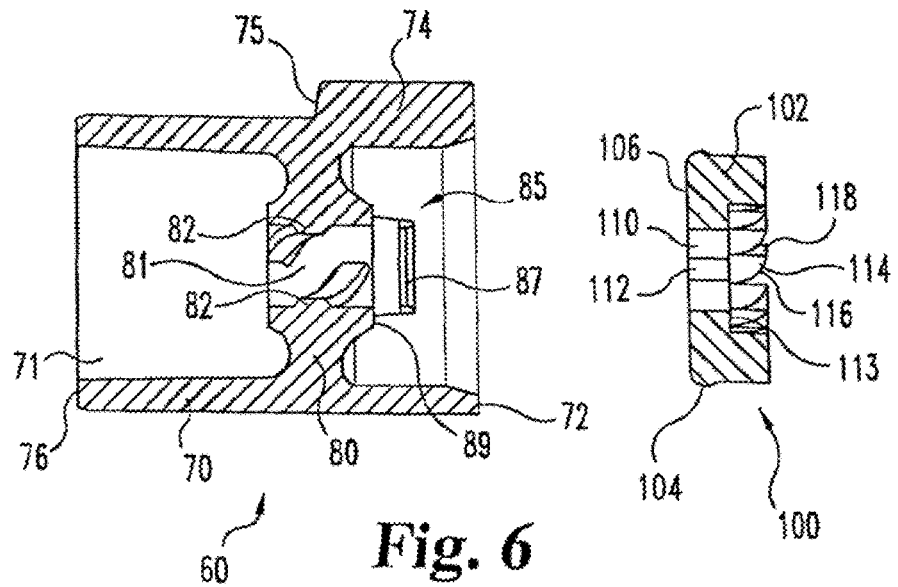
FIG. 6 is a cross-sectional view in exploded form of an injection nut and drive clutch of a drive assembly of the present invention.

In the embodiment of FIG. 3, drive clutch 100 of the inventive drive assembly is connected to floating nut 60 to be rotatably free and axially fixed. Drive clutch 100 has a disk shaped body 102 ringed completely by a radially outwardly projecting snap ring 104. When arranged as shown in FIG. 6 during the device assembly process, movement of drive clutch 100 toward nut 60 results in snap ring 104 ramping up the resilient clutch retainers 85 with the nut and clutch resiliently deforming slightly until snap ring 104 axially passes rim portions 87, at which time the pieces snap back to their original form to axially capture snap ring 104 between rim portions 87 and a protruding surface portion 89 of the proximal face of disk portion 80 which rings central opening 81. Protruding surface portion 89 has a smaller diameter than the distal surface 106 of drive clutch 100 to provide a smaller contact area to limit frictional resistance to rotation therebetween. Other types of latching mechanisms to axially retain the drive clutch within the floating nut while permitting relative rotation therebetween, including different numbers of rim portions or rearwardly extending, axially aligned prong portions from which a latch portion projects radially inward, also may be substituted in alternate embodiments.

Figure 5:
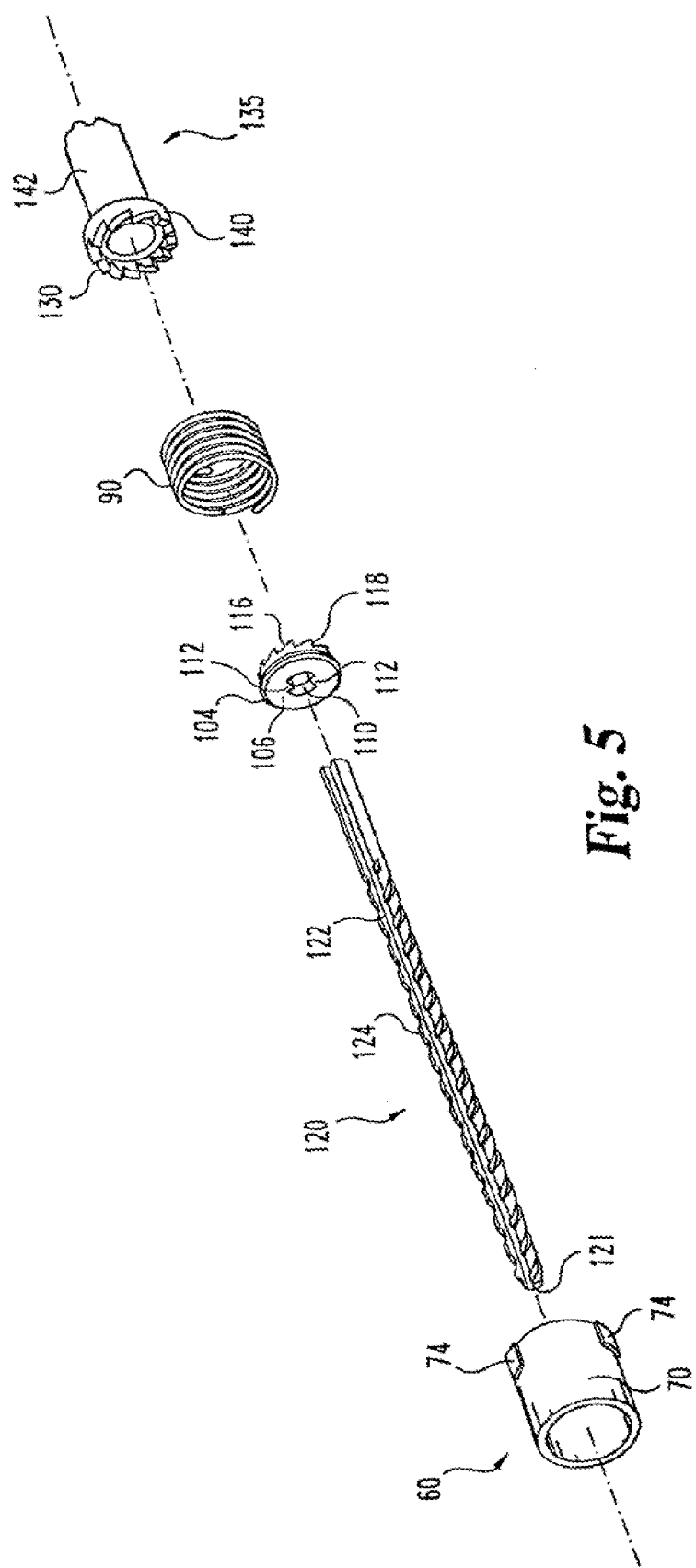
FIG. 5 is a perspective view of the drive assembly, and a rotatable drive member that powers drive assembly operation, removed from the injection pen of FIG. 1.

Body 102 of drive clutch 100 defines a central opening 110 and has at least one inwardly extending V-shaped portion or key 112 projecting within the opening. Key 112 fits within a corresponding keyway channel 122 longitudinally extending along the length of drive or lead screw 120, which includes external threading 124 that engages threading 82 of floating nut 60. As shown in FIG. 5, two diametrically arranged keys 112 fit within longitudinal keyways 122 located on opposite sides of the drive screw. The interfitting of keys 112 with keyways 122 causes forced rotation of drive clutch 100 during injection to rotate drive screw 120, and similarly causes forced rotation of drive screw 120 during reset to rotate drive clutch 100.

Drive clutch 100 is adapted to engage a rotatable drive member of the injecting mechanism for torque transmission. The outer radial region of proximal surface 113 includes a series of axially projecting, generally triangular shaped teeth 114 arranged in an annulus, which teeth are structured and arranged to mate with similarly configured teeth 130 provided on drive member 135. Each tooth 114 includes a ramped side 116, and an axially aligned side 118 to which force is directly applied by a tooth 130 during driving rotation of drive clutch 100 by drive member 135. In alternate embodiments, different torque transmitting configurations, including flat plates relying exclusively on friction for non-slipping torque transmission, may be substituted for the particular toothed configuration shown.

The rotatable drive member 135 rotates when injection pen 20 is operated to cause fluid to be ejected through needle assembly 27. Drive member 135 is diagrammatically shown as an annular disc 140 rotatably fixed to a sleeve 142 journaled within the injection pen and through which extends drive screw 120. Annulus 140 includes the forwardly extending teeth 130. The inventive drive assembly may be driven by differently designed rotatable drive members within the scope of the invention.

The inventive drive assembly will be further understood in view of the following explanation of aspects of the operation of injection pen 20, starting with the injection pen configured as shown in FIG. 2 which occurs when a new cartridge assembly 24 is replacing an exhausted cartridge assembly that is not shown. The user will first assemble cartridge assembly 24 to pen base 26.

Typically, a user will hold reusable pen base 26 in one hand, and cartridge assembly 24 in the other hand, and first maneuver the components such that distal end 121 of drive screw 120 is inserted within hub 46 and rod tip collar 38, and into contact with rod tip base disc 37. Pen base 26 and cartridge assembly 24 are then manually moved together in an axial direction until hub 46 is axially introduced into the pen base hollow interior and the external threads of stepped-down neck portion 44 initially abut internal threads 66 of cartridge interface portion 62. In the course of this movement, rod tip 35 is first moved farther into cartridge 22 to close up any spacing that may have existed between it and plunger 34, and then drive screw 120 is forced axially and screws through floating nut 60 while drive clutch 100 freely spins with drive screw 120 and within floating nut 60. The drive screw 120 is so pushed back or reset, rather than plunger 34 being forced to slide within cartridge 22, due to the relatively low frictional resistance to reset of the drive assembly.

To continue its mounting, cartridge assembly 24 is then rotated relative to pen base 26 to screw the components together. During an early stage of this rotation, within the housing interior volume, annular shoulder 45 contacts end surface 76 of floating nut 60 that is in a forward axial position due to biasing by spring 90. In alternate embodiments, other portions of the cartridge assembly, such as the rearward end of hub 46, may be the point of contact with nut 60. In addition, rather than a direct contact or engagement with the nut, the cartridge assembly may indirectly engage the nut, such as via an interposed member made of a low friction material. Continued screwing in of cartridge assembly 24 by the user shifts floating nut 60 rearward against a resisting force generated by the compressing of spring 90. In particular, shoulder 45 slides along floating nut end surface 76 as the cartridge assembly rotates and move axially, while nut 60 moves axially without simultaneously rotating. The resisting force generated by spring 90, which increases as the insertion progresses, reduces play between cartridge assembly 24 and pen base 26 to provide injection pen 20 with a more solid or well-constructed feel to a user, and to limit pen drooling that can occur during relative movement of the cartridge and the drive screw.

Figure 4:
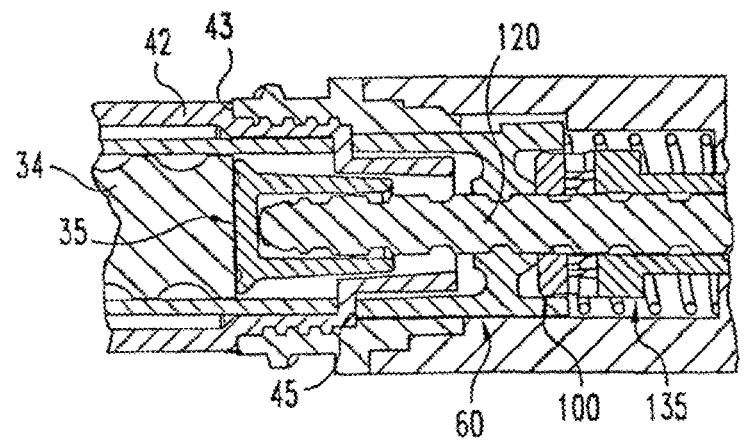
FIG. 4 is a fragmentary plan view in cross-section diagrammatically showing the injection pen of FIG. 1 with the cartridge assembly fully mounted to the reusable pen base.

Cartridge assembly 24 is fully mounted after it has been screwed in until end face 43 of barrel 42 abuts the distal face of cartridge interface member 62, which arrangement is shown in FIG. 4. When cartridge assembly 24 is so mounted, nut 60 and the retained clutch 100 are in a rearward axial position at which teeth 114 of drive clutch 100 are positively engaged with teeth 130 of drive member 135 in a non-slip fashion so clutch 100 can be rotated by rotation of drive member 135.

Subsequently, and with respect to the injection pen 20 shown in FIG. 1, after knob 28 has been dialed out to set a dose, the plunging of button 30, which is mechanically interconnected with sleeve 142 of drive member 135, rotates drive member 135 to rotate the drive clutch 100 and thereby drive screw 120, which screws out through nut 60 to advance plunger 34 to force medicine from the needle equipped cartridge assembly 24.

Figure 7:
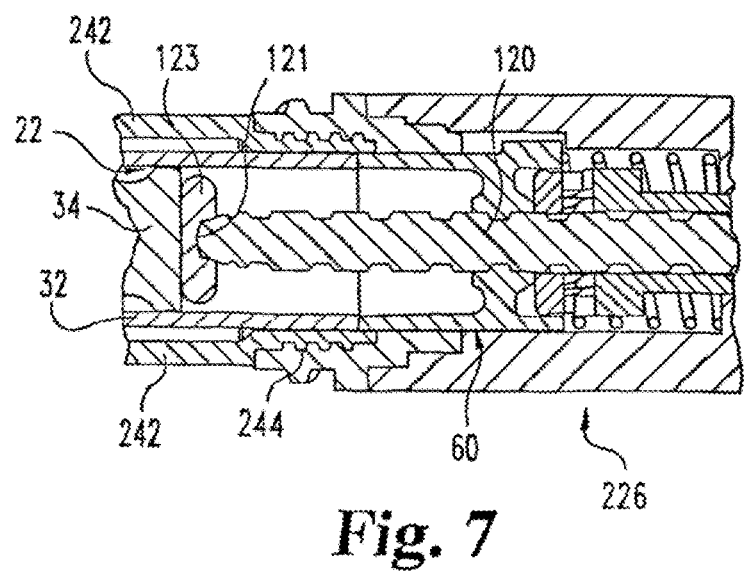
FIG. 7 is a fragmentary plan view in cross-section diagrammatically showing another injection pen in which an inventive drive assembly biases forward a cartridge within a retainer mountable to the pen base.

Referring now to FIG. 7, there are diagrammatically shown portions of another injection pen equipped with a drive assembly of the present invention. In this embodiment, the reusable pen base 226 is similarly constructed to that shown in FIG. 3, and further the drive assembly is the same as that shown in FIG. 3 other than end 121 of drive screw 120 being configured to rotatably support an added foot 123. Foot 123 is attached so as to be freely rotatable about the axis of screw 120 during use and serves to distribute pressure on plunger 34. The cartridge assembly in FIG. 7 is in the form of a reusable retainer 230 with a disposable cartridge loaded therein, which cartridge is similar to cartridge 22 but lacks a rod tip 35. Retainer 230 is connectable to the pen base housing such as via threads shown at 232. Cartridge 22 is insertable into, and removable for replacement from, the retainer through the open rearward end of the retainer when the retainer is not connected to pen base 226. When a retainer 232 with a loaded cartridge 22 is mounted to pen base 226, floating nut 60 directly contacts the cartridge housing 32, and the spring biasing of the nut forces cartridge 22 forward within the retainer against the interior surface of a not shown forward end of the retainer. Cartridge 22 is thereby prevented from moving relative to nut 60.

In still another alternate embodiment which is not shown, the drive clutch need not be held by the floating nut, but instead is simply shifted into engagement with the drive member by, for example, abutting contact with the floating nut. In such a configuration, the spring operably engages the drive clutch to bias it out of engagement with the rotatable drive member when no cartridge assembly is properly mounted to the pen base. For example, the forward end of a spring may abut a washer member which holds forward the drive clutch, such as in contact with the floating nut.

FIGS. 8-11 show injection clicker assemblies of the present invention, which assemblies may find beneficial application in injection pens, such as injection pen 20 of FIG. 1. However, and while descriptions of these assemblies below may make reference to such a pen 20 in general, such assemblies are not limited to being incorporated into pens similar to pen 20. The inventive injection clicker assembly may be readily adapted for many alternately configured injectors in view of the explanation herein, as the inventive injection clicker assembly described further below in theory may be mounted on rotatable drive sleeves of injecting mechanisms which are turned by operation of differently configured components of those injecting mechanisms. Additionally, the injection clicker assembly does not require the presence of a dose setting mechanism that allows variability in the quantity to be delivered.

Figure 8:
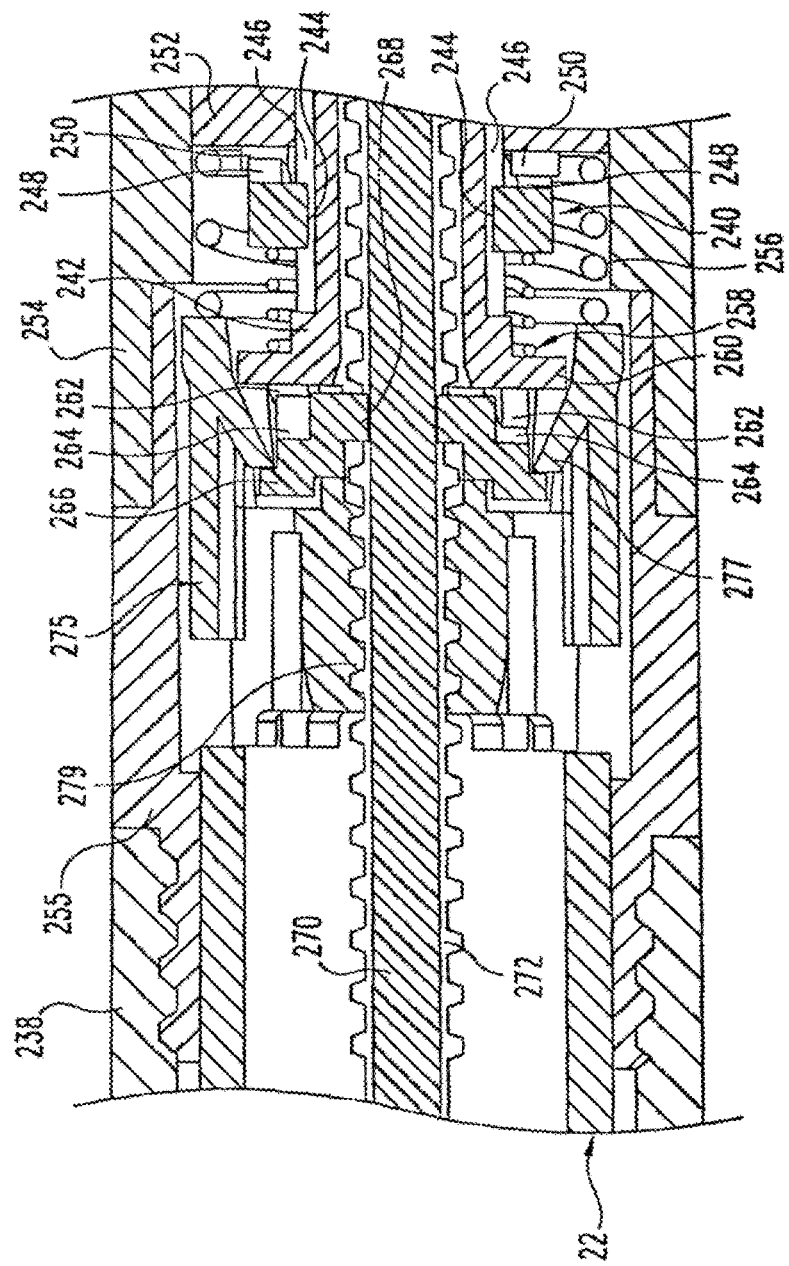
FIG. 8 is a fragmentary view in cross-section diagrammatically showing portions of an injection pen equipped with one form of an injection clicker assembly of the present invention.

As shown in FIG. 8, one form of the injection clicker assembly of the present invention includes a ring-shaped collar or clicker element, generally designated 240. In the description below of the operation of the pen portion shown in FIG. 8, such pen portion is described as being a part of pen 20 shown in FIG. 1 to facilitate explanation, but it will be appreciated that the pen shown in FIG. 8 includes, for example, a drive assembly which is slightly different than that which is described above with respect to pen 20, as well as a cartridge assembly that comprises a reusable retainer 238, which is threadably connected to the pen base housing, and a disposable cartridge 22 loaded therein.

Annular collar 240 defines a central bore through which drive sleeve 242 extends such that collar 240 is coaxially mounted on drive sleeve 242. At least one rib or key, such as a pair of diametrically opposed keys 244, inwardly project within the central bore of collar 240 and slidably fit within longitudinally extending slots or keyways 246 on opposite sides of drive sleeve 242. The keying of collar 240 with drive sleeve 242 results in collar 240 being rotatably fixed but axially movable relative to drive sleeve 242. In an alternate embodiment, collar 240 can be keyed to drive sleeve 242 with mating keys and keyways that are on the drive sleeve and collar respectively.

The proximal face of collar 240 is formed with a ring of axially extending teeth 248. Teeth 248 mesh with complementary teeth 250 that are molded into bulkhead 252. The number of collar teeth 248 and teeth 250 to which it engages need not be in a 1 to 1 ratio, as the clicker may have, for example, every other tooth removed. Bulkhead 252 is an additional component splined to the pen outer housing portion 254, which outer housing is shown as an assembly of multiple component parts, such that bulkhead 252 is rotatably fixed relative to the pen housing during injecting use of the pen. Bulkhead 252 is axially fixed in the embodiment of FIG. 8 by being pressed by a spring 256 against a lip portion of the pen outer housing. In alternate embodiments, mating teeth 250 may be part of a bulkhead integrally formed with the pen outer housing.

Teeth 248 and 250 are configured such that when in meshed engagement, only unidirectional rotation of collar 240 relative to bulkhead 252, and thereby to the pen housing, is permitted. During such relative rotation, the collar teeth 248, when traveling across teeth 250, generate audible clicking noises. The unidirectional rotatability of collar 240 allows it to function as an anti-backup mechanism for the drive sleeve and injection screw as described further below. In alternate embodiments in which no anti-backup feature need be performed by collar 240, teeth 248 and 250 may be differently configured so as to not prevent reverse rotation and to thereby allow bi-directional collar rotation.

Injection clicker 240 is biased in the proximal axial direction along drive sleeve 242 by a biasing element, generally designated 258. In the shown embodiment, the biasing element is a coiled compression spring made of metal which is coaxially mounted on drive sleeve 242, but other types of springs or materials of construction alternatively may be employed. During injecting use of the pen, spring 258 backs up collar 240 to provide injection clicks and rotational positioning. During manufacture, springs of various strength can be tested in order to select a spring that provides a suitable clicking noise without modifying either the bulkhead or the collar design.

The distal end of spring 258 abuts a proximal facing surface of a radially protruding disk portion 260 of drive sleeve 242. The distal facing surface of disk portion 260 includes a ring of axially extending teeth 262 that are used to transmit rotational motion of the drive sleeve to a drive assembly that advances the injection screw. In the shown embodiment, which is intended to be illustrative and not limiting, the drive assembly includes a clutch 266 with proximal teeth 264 that mate with disk portion teeth 262 when the pen is fully assembled as shown in FIG. 8. Clutch 266 is keyed to threaded injection screw 270 via keys 268 that fit within diametrically disposed keyways 272 longitudinally aligned along the screw that extends through drive sleeve 242. Clutch 266 is axially retained within, but rotatable relative to, a floating nut, generally designated 275, by way of tangs 277 that snap fit over the clutch during assembly. Floating nut 275 is keyed to the pen housing to be axially movable but rotatably fixed. Floating nut 275 is biased distally by spring 256 when cartridge retainer 238 and cartridge 22 is disassembled from the pen base so as to disengage the drive sleeve teeth 262 from clutch teeth 264 to allow injection screw reset. When floating nut 275 moves distally during pen disassembly, for an injecting mechanism shown in which the drive sleeve is not axially fixed, drive sleeve 242 is moved distally by the action of spring 258 against disk portion 260, but is prevented from engaging clutch 266 by the abutment of disk portion 260 against the not shown keys of pen housing portion 255 to which floating nut 275 is keyed.

The injection clicker assembly of FIG. 8 will be further understood in view of the following explanation of its operation within a pen such as pen 20. When pen 20 is in the configuration shown in FIG. 1, which is a ready state prior to dose dialing for injection, the teeth of drive sleeve disk portion 260 and clutch 266 are engaged, and the teeth of collar 240 and bulkhead 252 are engaged as shown in FIG. 8. During dose dialing or selection, spring 258 maintains collar teeth 248 in meshing engagement with bulkhead teeth 252. Due to the unidirectional rotatability of collar 240 and its keying to drive sleeve 242, this teeth meshing rotationally locks drive sleeve 242. With the drive sleeve assembly locked rotationally, the clutch 266, and therefore the drive screw 270 keyed thereto, cannot rotate, thereby providing an injection screw anti-back up feature. During the plunging of button 34 in the dose injecting process described above, drive sleeve 242, and thereby collar 240 keyed thereto, is caused to rotate in the direction permitted by the tooth configuration of collar 240. Rotation of disk portion 260 of drive sleeve 242 rotates clutch 266 and thereby drive screw 270, which screws through an internal threading 279 of nut 275 to advance in the distal direction to shift the movable plunger of cartridge 22 so as to force medication from an outlet of the cartridge. As collar 240 rotates, it oscillates axially, against a proximal directed force applied by spring 258, as its teeth ride over bulkhead teeth 250 and create audible clicks that indicate injecting operation.

Figure 9:
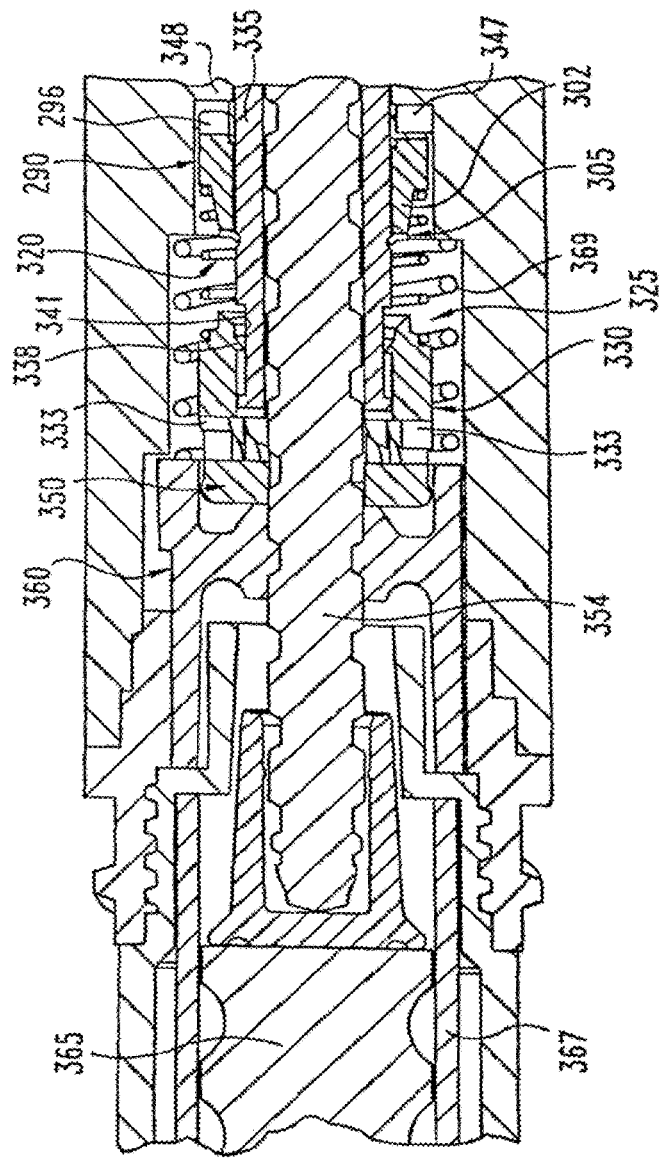
FIG. 9 is a fragmentary view in cross-section diagrammatically showing another form of an injection clicker assembly of the present invention within portions of another injection pen.
Figure 10:
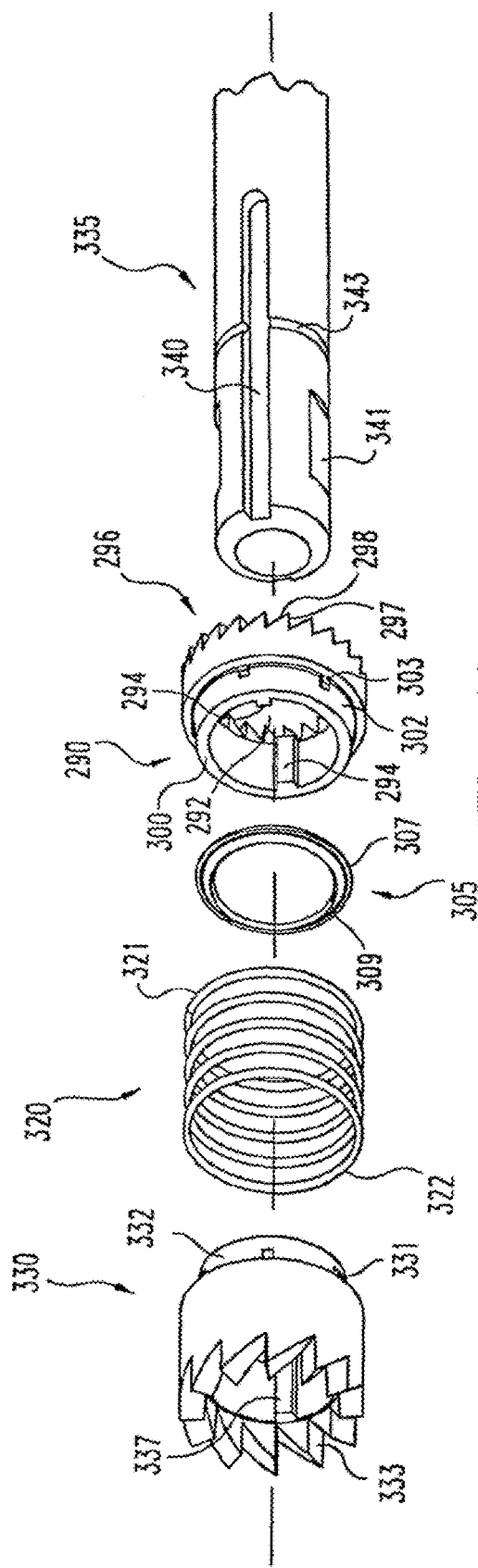
FIG. 10 is an exploded perspective view of the injection clicker assembly of FIG. 9 and portions of the injecting mechanism with which it interacts.
Figure 11:
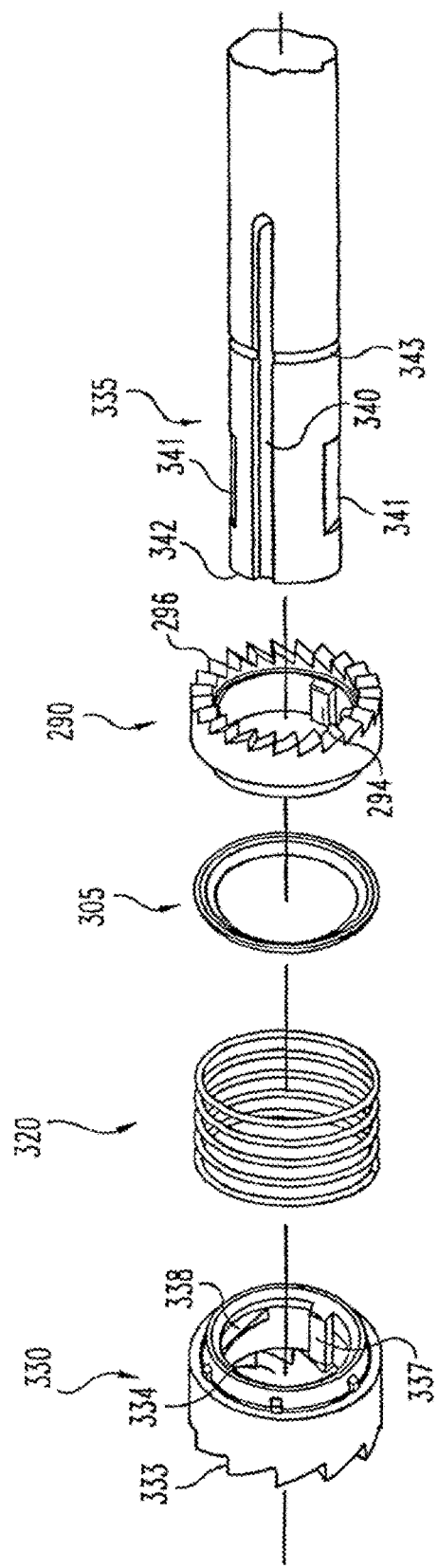
FIG. 11 is an opposite perspective view of FIG. 10.

Referring now to FIG. 9-11, another form of an injection clicker assembly of the present invention is shown in a different partially shown injection pen. This injection clicker assembly is particularly adapted for an injecting mechanism having a drive sleeve part that shifts axially during injecting operation. The injection clicker assembly includes a ring-shaped collar or clicker element, generally designated 290. Annular collar 290 defines a central bore 292 through which tubular base 335 of the drive sleeve extends. At least one rib or key, such as a pair of diametrically opposed keys 294, inwardly project within bore 292. Keys 294 fit within longitudinally extending keyways 340 on opposite sides of drive sleeve base 335 such that collar 290 is rotatably fixed but axially movable relative to the drive sleeve.

The proximal face of collar 290 is formed with a ring of axially extending teeth 296. Teeth 296 mesh with complementary teeth 347 molded into a bulkhead 348 integrally formed with the diagrammatically shown pen outer housing.

Each tooth of teeth 296 includes an axially aligned surface 297 and a ramped surface 298 extending to the axially aligned surface of the successive tooth, which teeth configuration permits unidirectional rotation of collar 290 relative to the pen housing that allows the collar to function as an anti-backup mechanism. During such relative rotation, the collar teeth 296, when traveling across the pen housing teeth 347, generate audible clicking noises.

Injection clicker 290 includes a distal surface 300 which at times during pen operation is abutted by a radially aligned, outer region 307 of a retainer ring, generally designated 305. Ring 305 includes a forwardly angled, central portion 309 which interference fits during pen assembly into a circumferential groove 343 formed in drive sleeve base 335. This connection causes retainer ring 305 to follow the axial movement of drive sleeve base 335 during operation, which axial movement is a function of the particular injecting mechanism of the pen. Retainer ring 305 serves to restrict axial motion of collar 290 when the drive sleeve is axially positioned as shown in FIG. 9, such as during dose dialing, by its outer region 307 engaging surface 300, thereby preventing the disengagement of collar teeth 296 from housing teeth 347.

Collar 290 is biased in the proximal axial direction by a coiled metal compression spring 320 coaxially oriented around drive sleeve body 335. The proximal end 321 of spring 320 fits around a stepped-down diameter neck portion 302 of collar 290. Spring end 321 is pressed over and retained by six ribs 303 spaced at even intervals around the neck portion circumference.

The distal end 322 of spring 320 fits around a stepped-down diameter neck portion 332 of a radially protruding, torque-transmitting member 330 of the drive sleeve, generally designated 325. Drive member 330 is the portion of the drive sleeve which transmits rotational drive sleeve motion to a clutch 350 keyed to drive screw 354. Six ribs 331 evenly spaced around neck portion 332 are pressed into the distal end 322 of spring 320 during pen assembly to retain spring 320 to drive member 330. The distal facing surface of drive member 330 includes distally, axially extending teeth 333 that mate with teeth on clutch 350 when the pen is assembled for use.

In the embodiment shown in FIGS. 9-11, the drive sleeve is a two part assembly, as radially protruding drive member 330 is configured to allow limited axial movement relative to tubular base 335 of the drive sleeve, which base is caused to rotate when the injecting mechanism of the pen is operated. This ability of relative motion aids in preventing clutch binding when a cartridge assembly is mounted to the pen base. In particular, during cartridge assembly mounting, in the condition that the clutch mechanism is meeting tooth to tooth, drive member 330 can back up allowing the cartridge assembly to be fully installed without locking up or damaging the clutch teeth, and any tooth to tooth condition that remains after installation is automatically addressed upon pen priming. This ability of relative motion also allows for the axial movement of the drive sleeve tubular base during injecting operation, which movement is a function of the overall injecting mechanism of the pen.

Within a central bore 334 of drive member 330 through which fits tubular base 335, a pair of diametrically opposed keys 337 project radially inwardly. Keys 337 fit within longitudinally extending keyways 340 such that member 330 is rotatably fixed but axially movable relative to drive sleeve base 335. A pair of diametrically opposed snaps or ribs 338 also project within bore 334 at locations offset ninety degrees from keys 337. During manufacturing assembly of drive member 330 to base 335, ribs 338 snap-fit into recesses 341 formed on the periphery of drive sleeve base 335 and in spaced apart relationship from distal end 342. Recesses 341 extend in the axial direction greater than the thickness of ribs 338 so as to permit the limited axial movement of drive member 330 relative to base 335. The snap-fit connection prevents the drive sleeve assembly from coming apart axially when a medication cartridge is disassembled from the pen base, and further insures that the forward travel of drive member 330 is limited by drive sleeve base 335 to aid in disengagement of drive member 330 from clutch 350 when a cartridge assembly is removed.

The teeth 333 of drive member 330 mate with a clutch of a drive assembly utilized to shift the injection screw distally. The drive assembly shown in FIG. 9 has a clutch 350 internally keyed to a threaded drive screw 354 that extends through drive sleeve base 335. Clutch 350 is connected to a rotatably fixed floating nut 360 which threadedly engages drive screw 354. Rotation of clutch 350 via the drive sleeve 325 rotates drive screw 354, which screws through nut 360 to advance in the distal direction beyond the end of the reusable pen base to shift movable plunger 365 of cartridge 367 so as to force medication from an outlet of the cartridge. Floating nut 360 is biased distally by spring 369 when the cartridge assembly is removed so as to disengage the drive assembly from drive sleeve teeth 333 to allow injection screw reset. This drive assembly is more fully described above. Other drive assemblies with a clutch that operably engages drive sleeve member 330 when the pen is assembled for use may be used in devices with the inventive injection clicker assembly.

The injection clicker assembly of FIGS. 9-11 will be further understood in view of the following explanation of its operation within the pen. When the pen is assembled as shown in FIG. 9, the teeth 333 of drive sleeve member 330 and clutch 350 are engaged and the teeth of injection clicker 290 and the pen housing are engaged. During dose dialing, drive sleeve base 335 is proximally retained, such as by a not shown spring, causing retainer ring 305 to abut collar surface 300 to keep clicker teeth 296 in meshed engagement with housing teeth 347. Due to the keying of collar 290 to drive sleeve base 335, this teeth meshing rotationally locks the drive sleeve base 335, and therefore the drive member 330 due to its keying to base 335. With the drive sleeve assembly locked rotationally, the clutch 350, and therefore the injection screw 354 keyed thereto, cannot rotate, thereby providing an injection screw anti-back-up feature.

When the injecting mechanism is manually operated during an injecting use of the dialed up pen, drive sleeve base 335 first moves distally to shift retainer ring 305 distally such that collar 290, subject to overcoming the biasing force of spring 320, is movable distally. The drive sleeve body 335 then begins to rotate, and teeth 296 of collar 290 shift in and out of engagement with the housing teeth producing injection clicks. The drive sleeve rotation also causes the drive clutch 350 to rotate which screws the injection screw 354 through floating nut 360. During this injecting process, if the floating nut floats proximally slightly, the compressed spring 369 forces it back toward the pen distal end to finish the injection.

Figure 12:
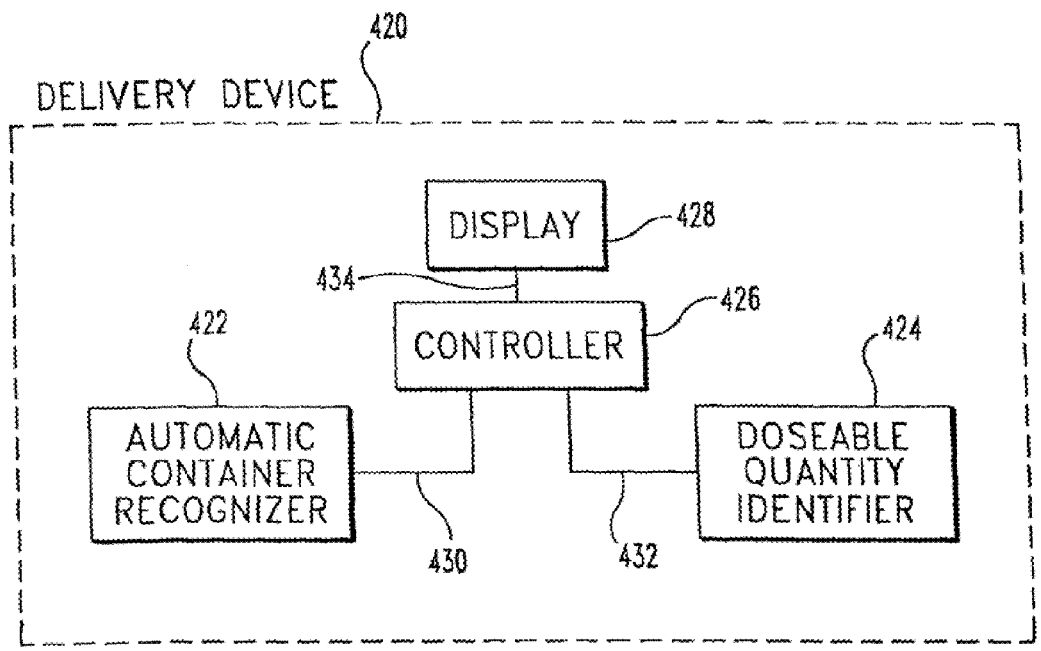
FIG. 12 is a block diagram representation of one form of a therapeutic dose indicating apparatus of the present invention.

In one form shown in block diagram in FIG. 12, a therapeutic dose indicating apparatus of the present invention is housed in a delivery device 420 and utilizes an automatic container recognizer 422, a doseable quantity identifier 424, a controller 426, and a display 428. One type of delivery device for which the system is particularly well suited is an injection pen, but other types of portable devices, such as a pulmonary device or inhaler, may be similarly equipped.

Automatic container recognizer 422 functions first to recognize a characteristic of a container insert into delivery device 420, which characteristic in one embodiment relates to a concentration of the medicine within the container, and then to input that information to controller 426 as shown at 430. Doseable quantity identifier 424 functions first to sense the arrangement to which the dose setting mechanism of delivery device 420 has been manipulated by a user to prepare the device to deliver a finite volume of medicine, and then to input that information to controller 426 as shown at 432. In response to the input information, controller 426 calculates the therapeutic dose to be delivered and instructs display 428 via line 434 to visibly display that dosage to a user of delivery device 420.

Figure 13:
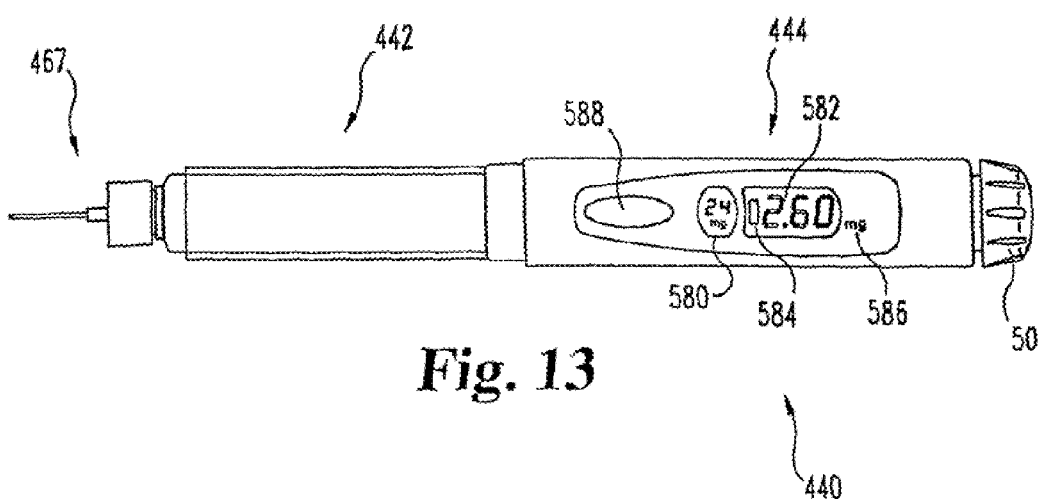
FIG. 13 is a diagrammatic plan view of an injection pen as the delivery device equipped with one form of the therapeutic dose indicating apparatus shown in FIG. 12.

The delivery device with therapeutic dose indicating capabilities of FIG. 12 is shown in FIG. 13 as a reusable injection pen, generally designated 440. As is conventional in reusable devices of its type, injection pen 440 includes a cartridge assembly, generally designated 442, which is connected to a pen base, generally designated 444, which houses dose setting and injecting mechanisms that when operated cause a quantity of medicine to be selected and then expelled from cartridge assembly 442 through injection needle assembly 467.

Figure 14:
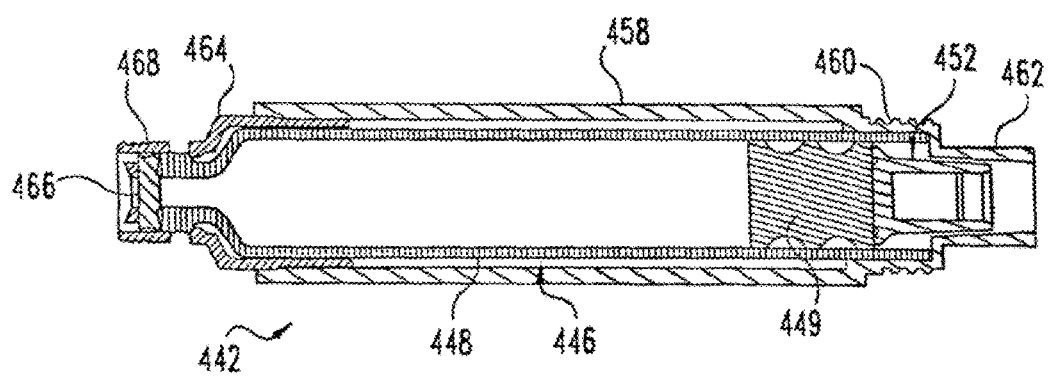
FIG. 14 is a cross-sectional view of a cartridge assembly removed from the injection pen of FIG. 13.

One form of cartridge assembly 442 is further shown in cross-sectional view in FIG. 14 and is, but for the identifier described below, the same as the cartridge assembly 24 of FIG. 2. Thus, cartridge assembly 442 includes a cartridge 446 with a glass housing 448 that defines a medication-filled internal volume. The cartridge includes slidable plunger 449, rod tip 452, cap 464 and septum 466. Cartridge 446 is further protected by an outer housing or barrel 458 that includes an externally threaded, stepped-down neck portion 460, and a further stepped-down rear hub 462. External threads 468 on cap 464 allow mounting of injection needle assembly 467 that pierces septum 466.

The automatic container or cartridge recognizer 422 of injection pen 440 includes an identifier associated with cartridge assembly 442 which is designed to work with a sensor that signals controller 426 within pen base 444 based on the identifier sensed. As described in U.S. Pat. Nos. 5,954,700 and 6,110,152, the disclosure of which are hereby incorporated herein by reference in their entirety, the identifier can take many forms and be used to indicate a variety of facts to the user.

In one form, the identifier is used to represent the concentration of the therapeutic contents of the cartridge assembly, and which concentration identifier is disposed on the outer housing hub 462 of cartridge assembly 442. The concentration identifier possesses specific characteristics, such as dimensional and spatial characteristics, recognizable by the sensor of automatic cartridge recognizer 422. In alternate embodiments, and with corresponding modifications to the sensor of automatic cartridge recognizer 422, the identifier may be placed on other portions of the cartridge assembly, including but not limited to cartridge housing 448, and rod tip 452, and further may be used to represent, for example, which one of different possible insulin types is contained in the cartridge assembly.

The concentration identifier is permanently affixed to the cylindrical exterior surface of hub 462. For cartridge recognition systems that sense or otherwise read the identifier with elements other than radially outwardly located electrical contacts as described below, for example when the concentration identifier is adapted for use with optical or magnetic sensors, the identifier need not be exposed on the periphery of hub 462, and may be differently positioned such as affixed to the interior surface of hub 462.

As further illustrated in the various embodiments shown and described with reference to FIGS. 15-17, the cartridge concentration identifier is shown formed by a single strip of electrically conductive material fixedly associated with hub 462. The shown strip extends the entire hub circumference, but may span only a part of the circumference if the associated sensor contacts of container recognizer 422 described below are configured to achieve a satisfactory connection despite one or more circumferential gaps in the strip. The conductive strip may be in the form of a pad printed conductive ink applied to the hub, however, other means of accomplishing the identifier strip may be employed. For example, the strip may be a crimped metal band, or a conductive electroplating of a material insert molded into the hub, or a conductive paint, or a pad printed ink, or a metallic self-adhesive label, or a non-conductive adhesive label onto which an appropriate electrically-conductive pattern has been applied.

Figure 15:
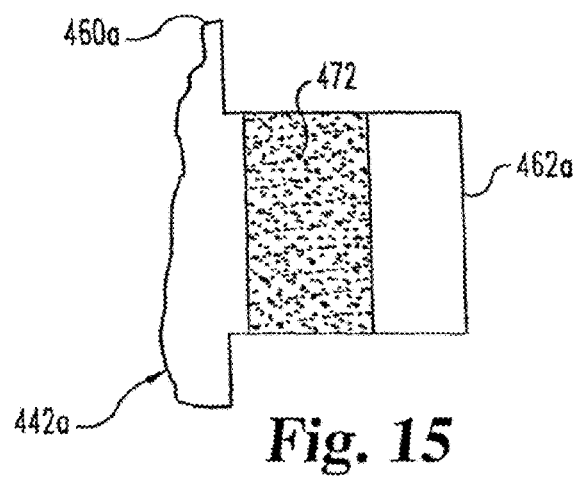
FIG. 15 is a plan view of a first embodiment of a barrel hub of the cartridge assembly of FIG. 14.
Figure 16:
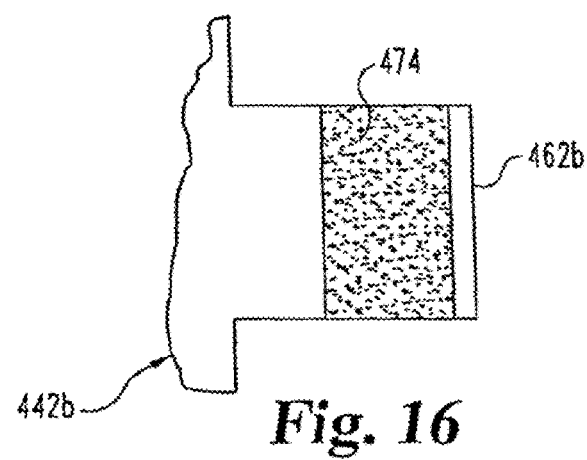
FIG. 16 is a plan view of a second embodiment of a barrel hub of the cartridge assembly of FIG. 14.
Figure 17:
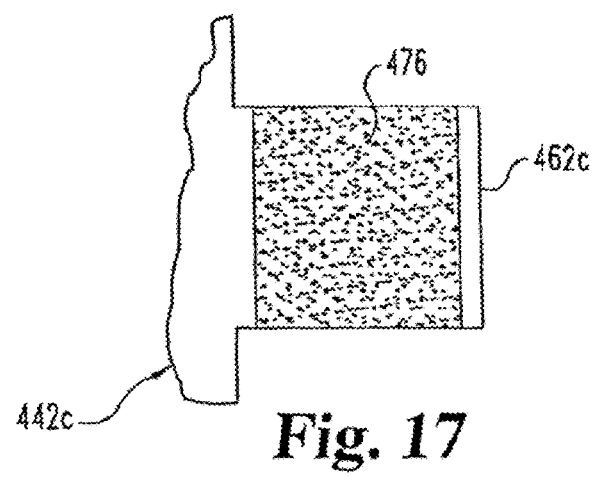
FIG. 17 is a plan view of a third embodiment of a barrel hub of the cartridge assembly of FIG. 14.

Referring now to FIGS. 15-17, hubs 462a, 462b and 462c of three different cartridge assemblies 442a, 442b and 442c each compatible with pen base 444, are shown. The type of content identifier shown being used on hubs 462a, 462b and 462c uses the dimensional aspect of the width of the conductive strip, along with the spatial aspect of the placement of that strip on a hub, to represent the cartridge contents. This type of content identifier has particular applicability to identifying the concentration of hGH, which has a limited number of common concentrations, and therefore the three cartridge assemblies shown in FIGS. 15-17 each contain hGH in a different concentration. In other types of content identifiers within the scope of the invention, the dimensional aspect of the identifier strip may be different than the width, such as the thickness or texture of the strip.

In FIG. 15, representing a first concentration, a conductive strip 472 having a relatively small width, such as about 4.8 mm, encircles hub 462a of cartridge assembly 442a near the distal end of the hub which is adjacent the threaded neck 460a of the barrel. In FIG. 16, representing a second concentration, a conductive strip 474 having a relatively small width, such as about 4.8 mm, encircles hub 462b of a second cartridge assembly 442b near the proximal end of the hub. Although the widths of strips 472 and 474 are identical to reduce the number of differently constructed parts needed for manufacture of the various cartridge assemblies, as will be appreciated from the explanation of the device operation that follows, different widths for strips 472 and 474 may be utilized so long as appropriate electrical circuits between the sensors result. Finally, in FIG. 17, representing a third concentration, a conductive strip 476 having a relatively large width, such as about 7.1 mm, encircles hub 462c of a third cartridge assembly 442c and covers nearly the entire hub axial length. The axial region of hub 462c covered by strip 476 is the same as would be covered by strips 472 and 474 if positioned on hub 462c at the same locations as such strips are positioned on hubs 462a and 462b, respectively.

Once any of the cartridge assemblies shown in FIGS. 15-17 has been properly mounted to injection pen 440, such as by screwing that cartridge assembly into pen body 444 of FIG. 13, the content identifier of that mounted cartridge assembly provides a conductive path between a series of sensor contacts within the device which are spaced along the axial length of the inserted hub. The varying widths and locations of the content identifiers of the various cartridge assemblies provide different conductive paths between the sensor contacts.

Figure 18:
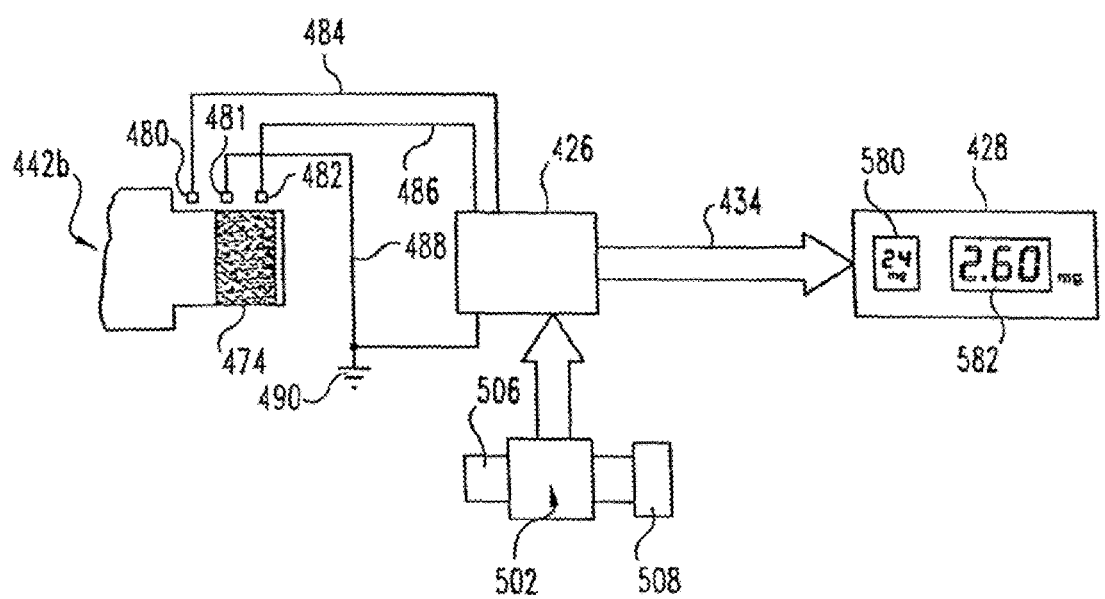
FIG. 18 is a schematic representation of how one form of the therapeutic dose indicating apparatus of the present invention operates.

For example, as schematically shown during operation in FIG. 18, the sensor includes electrical contacts 480, 481 and 482. Although these sensor contacts are shown in FIG. 18 as being in exact axial alignment, each of sensor contacts 480-482 may be angularly spaced from the other sensor contacts, such as within a 60° circumferential span or 120° apart, or such other angular spacing as may be possible within the pen base interior hollow. Furthermore, each sensor contact naturally could comprise a plurality of contacts circuited in parallel and positioned at the same axial hub location. The sensor contacts may be resilient metal fingers extending from a subassembly base pivotally mounted to, for example, the housing, and circuitry on the base is electrically connected to a circuit board of controller 426. The subassembly base is rotationally biased such that hub contact portions of the metal fingers are in a radially retracted position when no cartridge assembly is mounted to pen base 444. When the hub is inserted during connection of cartridge assembly 442 to pen base 444, through movement of the hub, or of a movable part of the pen base engageable with the hub, such as a floating nut described above, a pivot arm of the subassembly base is contacted, causing the subassembly base to rotate such that the contact portions of the fingers are moved into communication with the content identifier. In an alternate embodiment, rather than pivotable sensor contacts, the fingers may be resilient or leaf spring type metal fingers which are biased radially inward into contact with the hub and which are mounted, for example, to the pen base housing or to a part movable within the housing of pen base 444 itself, which fingers slide along the hub as the hub inserts during connection of cartridge assembly 442 to pen base 444.

Controller 426 processes the data related to which of the sensor contacts within injection pen 440 are in communication with the conductive strip of the content identifier and derives information from a look-up table to essentially read what is represented as being within the cartridge assembly. For example, sensor contacts 480 and 482 are directly circuited with controller 426 by lines 484 and 486, which lines may be patterns imprinted on a circuit board of controller 426. Sensor contact 481 is similarly circuited to controller 426 by line 488 which is grounded at 490. When cartridge assembly 442b with content identifier 474 is loaded as shown in FIG. 18, grounded sensor contact 481 is in communication with identifier 474, and the conductivity of identifier 474 is used to ground sensor contact 482 and thereby line 486 to controller 426. Because sensor contact 480 is not in communication with identifier 474, line 484 is not grounded. As a result, controller 426 is effectively signaled that line 484 remains open while line 486 has been closed, and controller 426 equates this input to a certain hGH concentration, such as 12 mg, being present within the loaded cartridge assembly 42b. (This concentration, as well as other hGH concentrations referred to herein, is indicated in mg units, as opposed to mass per volume units as might otherwise be expected, because that is how these concentrations for hGH are normally referenced, such as by physicians to their patients. Such an indication is a result of the numeric value relating to the mass in mg of lyophilized drug before its reconstitution, which results in the cartridge contents being in liquid form. The concentration in mg/ml can be readily obtained by dividing the referenced milligram mass by the 2.88 milliliter volume of the cartridge contents when reconstituted.) In a similar manner, when cartridge assembly 442a with content identifier 472 is loaded, grounded sensor contact 481 is in communication with identifier 472, and identifier 472 is used to ground sensor contact 480 and line 484 to controller 426, but sensor contact 482 and line 486 is not grounded, thereby resulting in controller 426 being signaled that line 486 remains open while line 484 has been closed such that controller 426 equates this input to a different hGH concentration, such as 6 mg, being present within the loaded cartridge assembly 442a. Similarly, when cartridge assembly 442c with content identifier 476 is loaded, grounded sensor contact 481 is in communication with identifier 476, and identifier 476 is used to ground sensor contacts 480 and 482 and lines 484 and 486 to controller 426, thereby resulting in controller 426 being signaled that lines 484 and 486 have each been closed such that controller 426 equates this input to a different hGH concentration, such as 24 mg, being present within the loaded cartridge assembly 442c. Finally, when no cartridge assembly is loaded, or a cartridge assembly without an identifier or with a defective identifier is loaded, controller 426 is signaled that lines 484 and 486 each remain open such that no concentration information is available as input.

It will be appreciated that the cartridge recognition system could have more or less than the three contact points shown in FIG. 18, and could use recognizable electrical signals other than ground, such as a small voltage, to activate the content identifiers. In addition, in other forms of the present invention, the cartridge assembly may be differently configured such as is known in the art, and such as described above. In an embodiment where a disposable cartridge and a reusable retainer is used, the content identifier will be provided on the disposable cartridge, and pen base 444 will be correspondingly modified to permit recognition of that cartridge, such as by incorporating part of the recognition system, for example electrical contacts and wiring, into the retainer, or by configuring the pen base components, such as the contacts, to extend within the chamber of the retainer.

Figure 19:
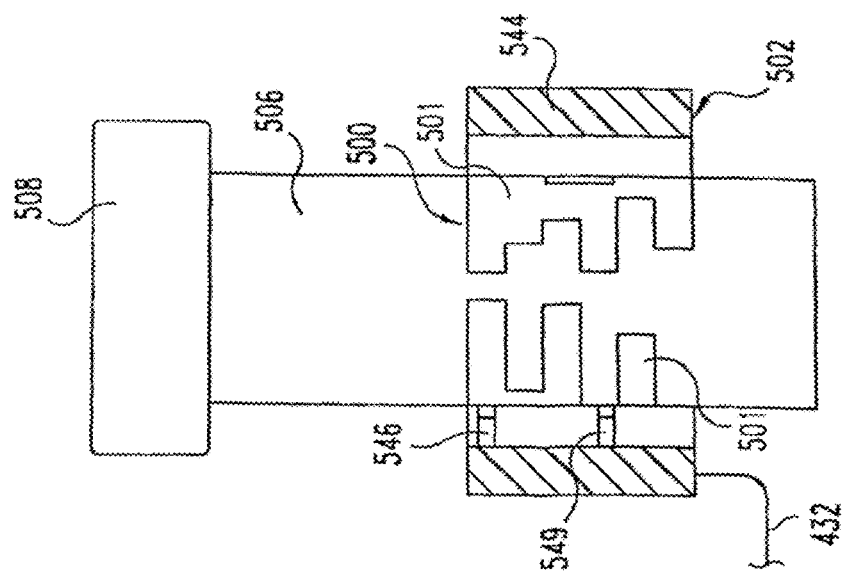
FIG. 19 is a diagrammatic plan view in partial cross-section of a sensor array and a dial-mounted rotational matrix of one form of a doseable quantity identifier of the present invention.

Referring now to FIG. 19, one form of a doseable quantity identifier of injection pen 440 is diagrammatically shown. Doseable quantity identifier 424 includes a rotational matrix, generally designated 500, and a sensor array, generally designated 502, which together are arranged to identify adjustments of the pen mechanism used at least in dose setting, as well as preferably in dose injecting after its dose setting. A variety of mechanisms for setting and injecting a dose are known in the injection pen art and are therefore not explained in exhaustive detail herein. Moreover, as the inventive doseable quantity identifier may be readily adapted for such and newly developed mechanisms in view of the explanation herein, the particulars of such mechanisms explained further herein are intended to be illustrative and not limiting. Furthermore, in alternate embodiments of the invention in its most general form, doseable quantity identifiers of known design which communicate with a controller may be substituted for the rotational matrix/sensor array within the therapeutic dose indicating apparatus of the present invention.

Rotational matrix 500 and sensor array 502 are operably connected to first and second components of injection pen 440 which experience relative rotational motion during operation of the dose setting mechanism by a user to select a volume desired to be injected.

In the embodiment of FIG. 19, the dose setting mechanism includes a rotatable dial 506 into which is incorporated rotational matrix 500. Dial 506 is rotationally fixed to an exposed knob 508 that is rotatable by the user to select the dose to be delivered by use of the injection pen. In the described embodiment, dial 506 when rotated via knob 508 translates out of pen base 444, or to the right from the perspective of a FIG. 13 viewer, during the dialing up of a dose in preparation for dose injecting. However, the inventive matrix need not be on a dial that so translates, but may be on another rotatable component such as a drive sleeve. In addition, although only one of the first and second relatively rotatable pen components is part of the dose setting mechanism in the embodiment of FIG. 19, as the other of these components to which sensor array 502 is connected may be the outer housing of pen base 444, the first and second components each may be parts of the dose setting mechanism in other embodiments.

Figure 20:
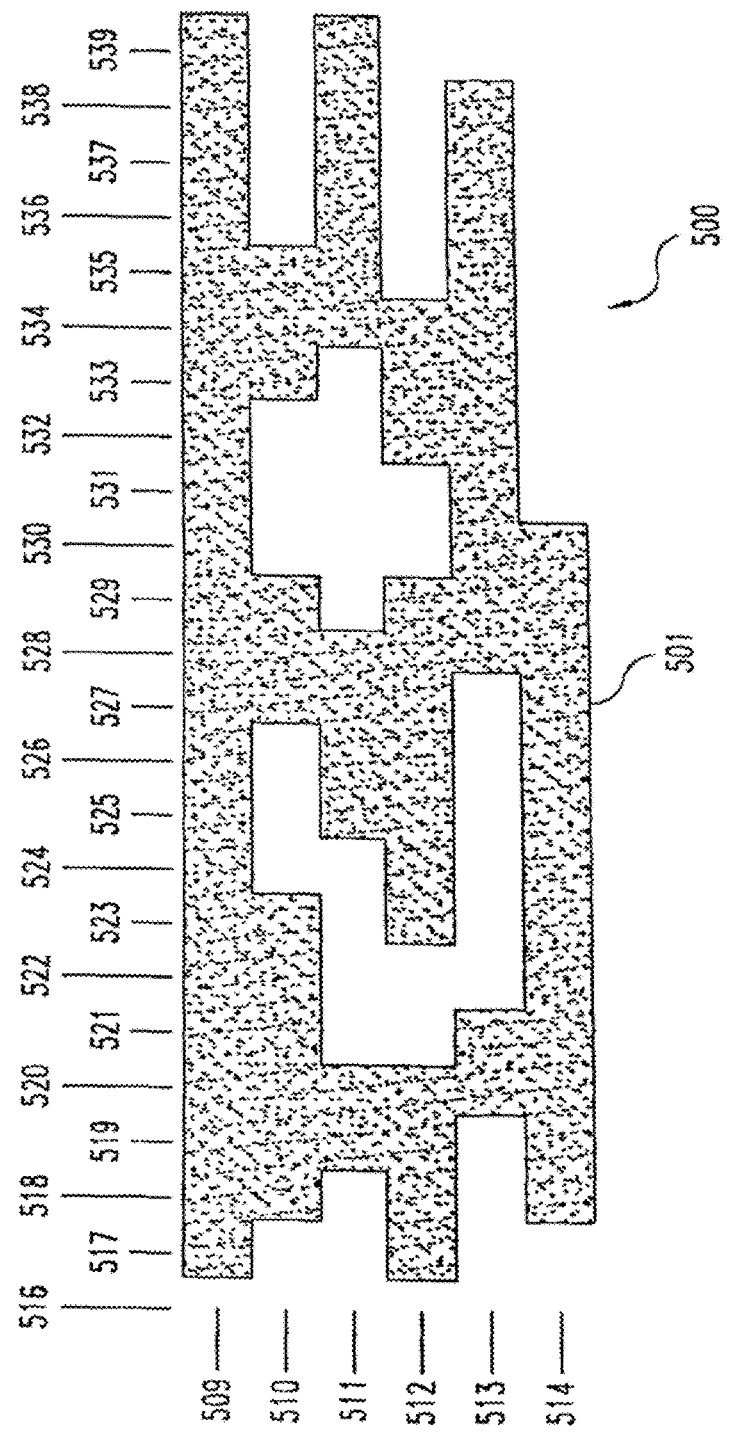
FIG. 20 is a plan view of the rotational matrix of FIG. 19 shown unwrapped and removed from the dose setting dial.

Shown removed from dial 506 and two-dimensionally in FIG. 20, matrix 500 is data arranged in a rectangular array formed of multiple orthogonally intersecting rows and columns. The number of columns is a function of the internal workings of the injection pen, and corresponds to the number of rotational positions within one of its revolutions at which dial 506 can be set to have the injection pen deliver different volumes of medicine. The movement of dial 506 between adjacent rotational positions corresponds to a change by one dose volume unit of the quantity to be injected by pen operation, and such change is known as a "click" due to the setting mechanism, as a result of its configuration, producing an audible click-like noise during such movement. The actual quantity of such dose volume unit, for example 0.024 ml, is a function of the design of the dose setting mechanism as is known in the art.

The data populating matrix 500 is in the form of the presence or absence of an electrically conductive material at the intersections of the rows and columns, which electrically conductive data points are shown contiguous or all linked to form a pattern 501 structured and arranged in conjunction with the sensor contacts of array 502 to convey information to controller 426 of pen 440. The linking allows an electrical signal delivered to a single data point on pattern 501, such as a grounding of that point, to travel along the entire pattern as described further below.

Each of the six rows 509, 510, 511, 512, 513 and 514 of matrix 500 extends around the entire circumference of dial 506. The twenty-four matrix columns 516, 517, 518, 519, 520, 521, 522, 523, 524, 525, 526, 527, 528, 529, 530, 531, 532, 533, 534, 535, 536, 537, 538 and 539 are equal width, so as each to span 15° of the dial circumference, and are aligned in parallel with the axial length of dial 506. In the shown embodiment, column 516 is unpopulated by any electrically conductive data points and is formed by a circumferential gap between the ends of the conductive pattern portion that otherwise fills row 509 (i.e. columns 517-539) when matrix 500 encircles dial 506. The twenty-four column matrix design permits twenty-four distinct rotational positions of dial 506 to be recognized. However, fewer or additional columns than the twenty-four shown may be provided within the scope of the invention. In addition, matrix rows different in number than the six shown may also be used as long as a suitable pattern recognizable by controller 526 results.

The electrically conductive pattern 501 of matrix 500 may be fabricated by two-shot molding a platable material, such as filled styrene plastic, into an electrically non-conductive or insulating sleeve, which molded material is then plated with a conductive material, such as successive layers of copper, nickel and then gold, so as to be electrically conductive. After plating, the sleeve is fixedly attached to dial 506. To facilitate manufacture, such as to provide a fixturing point needed to position the required pattern, the conductive pattern 501 of matrix 500 may include a not shown extension beyond the matrix rows or columns, but which extension is not used by sensor array 502. In alternate embodiments, the matrix pattern may be otherwise manufactured, such as a sheet metal matrix insert molded onto a sleeve, or such as in ways similar to those described above with reference to the cartridge content identifiers, for example via a metallic pattern on a non-conductive self-adhesive label or flexible circuit board attached to the dial, or by conductive paint or pad printed conductive ink applied directly to the dial.

Figure 21:
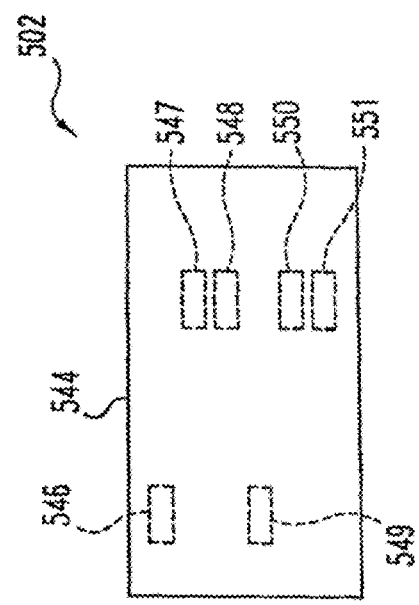
FIG. 21 is a plan view of the sensor array removed from the dial-mounted matrix of FIG. 19, wherein the sensor contacts are shown in dashed lines.

Sensor array 502 operationally engages matrix 500 to sense the matrix data. For the electrically conductive matrix pattern 501 shown in FIGS. 19 and 21, sensor array 502 includes resilient or leaf-spring type metal contacts 546, 547, 548, 549, 550 and 551 which extend radially inward from a cylindrical base sleeve 544 coaxially arranged on dial 506. Each of sensor contacts 546-551 abuts matrix 500 within a different row, and in the shown embodiment sensor contacts 546, 547, 548, 549, 550 and 551 are respectively aligned with matrix rows 509, 510, 511, 512, 513 and 514. Sensor contacts 546 and 549 are installed at a first circumferential position of base sleeve 544, sensor contacts 547 and 550 are installed at a second circumferential position of base sleeve 544 which is spaced 120° from the position of contacts 546 and 549, and sensor contacts 548 and 551 are installed at a third circumferential position of base sleeve 544 which is spaced 120° from the positions of both contacts 546 and 549, and contacts 547 and 550. This even angular spacing of the sensor contacts around the matrix serves to center the matrix and limit frictional resistance. For this 120° spacing, when dial 506 is rotationally oriented relative to sensor array 502 such that contacts 546 and 549 each abut matrix 500 within, for example, column 516, contacts 547 and 550 each abut matrix 500 within column 524, and contacts 548 and 551 each abut matrix 500 within column 532.

When sensor contact 546, which serves as the grounding contact as described below, is aligned with column 516, in the shown embodiment this is the "home" or "zero" position of the dial. When the pen is manipulated such that no volume of medicine will be delivered if the injecting mechanism of the pen is operated, the dial will be in this home position. At the home position, the ground is not electrically connected with any of the other contacts 547-551. The matrix pattern can be adapted to indicate this home position even if, for example, the conductive pattern filled all of row 519 including column 516. For such a matrix pattern, the pattern would also be configured to not be in contact with any of the other sensor contacts 547-551 when sensor contact 546 was aligned with column 516.

Matrix pattern 501 shown in FIG. 20 is designed complementary to this contact arrangement. Matrix pattern 501 uses a gray code coding scheme to reduce the risk of an error in dial position sensing going undetected. In the gray code coding scheme, the pattern is configured in view of the sensor positioning such that rotational dial movement, in either direction and in an amount equal to one column, causes only a single one of sensor contacts 547-551 to switch its electrical circuiting relationship with the pattern, which single switching can be monitored by the controller (i.e. only one sensor contact changes from being out of contact with the pattern to being in contact with the pattern, or vice versa, when dial rotation causes each sensor contact in its respective given column to be moved to a column on either side of that given column). In the shown embodiment, each of the twenty-four rotational set positions of dial 506 relative to sensor sleeve 544 results in a unique set of information being recognized by operation of sensor contacts 546-551.

It will be appreciated that column positionings of the sensor contacts different than the three 120° spaced sets described above may be used, for example all of sensor contacts 546-551 being aligned with one of the matrix columns, as long as appropriate modifications are made to the conductive matrix pattern.

To maintain the proper alignment of the sensor contacts with matrix pattern 501, sensor array 502 and rotational matrix 500 are rotatably free and axially fixed relative to one another. For the sensor array/rotational matrix shown in FIG. 19, sensor array 502 may be keyed to, for example, the housing of pen base 444 so as to be free to translate with, but not rotate with, dial 506 when the dial is rotated and thereby caused to translate during dose setting. Not shown connections between dial 506 and sensor array 502 may be used to cause sensor array to translate with the dial.

Sensor contacts 546-551 of array 502 are each circuited to controller 426 as abstractly represented at line 432 such that sensor input can be used by controller 426 to derive the matrix positioning using a look-up table in a similar manner as described above with respect to the automatic container recognizer. For example, during use a ground signal is sent to sensor contact 546, which is in contact with and grounds matrix pattern 501 at all rotational dial positions except when sensor contact 546 is aligned in matrix column 516. When electrically conductive matrix pattern 501 is so grounded, each of sensor contacts 547-551 that is in contact with conductive matrix pattern 501 is also grounded. The set of grounded/ungrounded signals received by controller 426 via line 432 for all of the sensor contacts is used to derive the rotational position of the matrix 500, and thereby dial 506, relative to sensor array 502. When sensor contact 546 is aligned with matrix column 516, none of the contacts are grounded, which information also is recognized by controller 426 as indicative of a particular one of the twenty-four rotational positions of dial 506.

The data of matrix 500 including areas of electrically conductive material is due to such data serving to complete electrical circuits with electrical contacts of the sensor. In alternate embodiments, different matrix data forms may be used with corresponding modifications to the sensor array. For example, if optical or magnetic sensing elements are to be employed in sensor array 502, the matrix data may be markings or magnets, as appropriate.

The matrix/sensor array shown in FIG. 19 is merely one suitable form and may be differently arranged within the scope of the present invention. For example, the locations of the sensor array and matrix may be reversed, such that a sensor array 502 circuited to controller 426 is mourned on dial 506 and arranged to engage a rotational matrix disposed on the inner circumference of coaxial sleeve 544.

Figure 22:
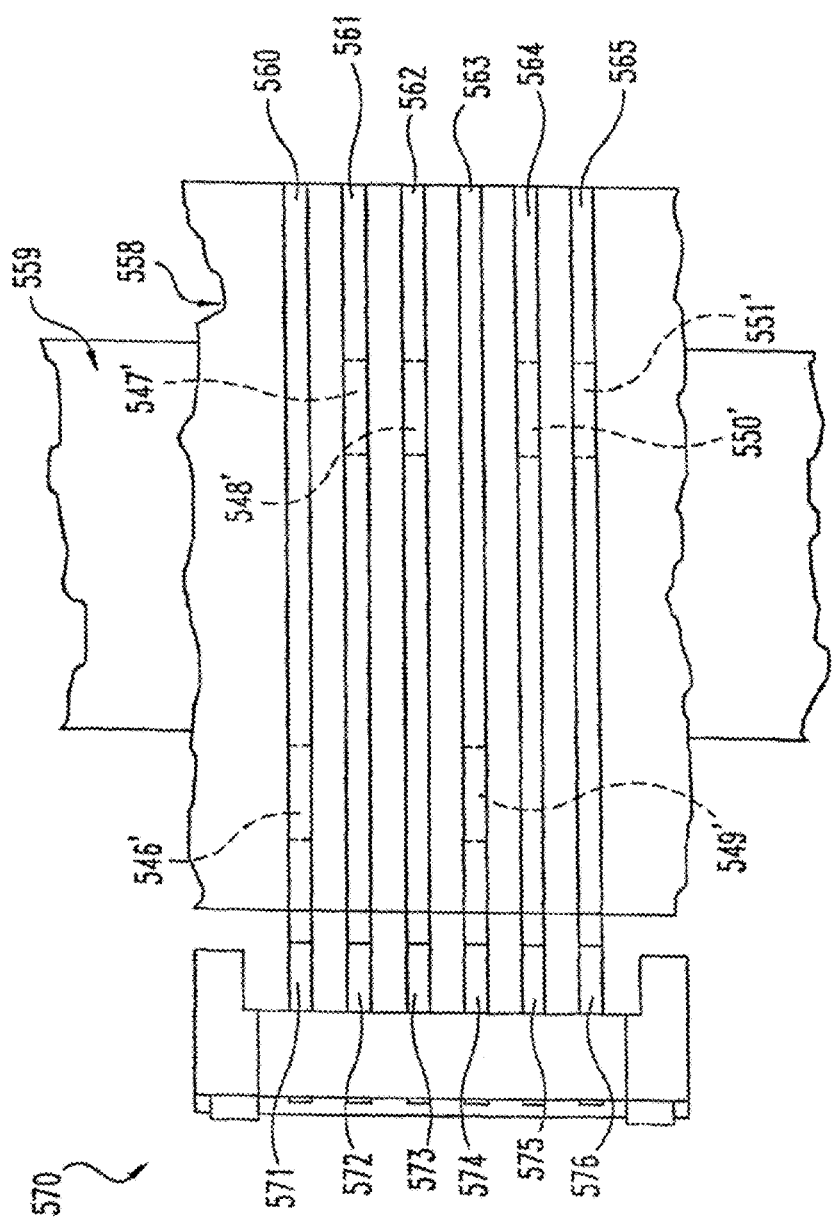
FIG. 22 is a plan view of another embodiment of a doseable quantity identifier of the present invention.

In addition, and as further described with reference to the embodiment of FIGS. 23-30, both the matrix and sensor array may be disposed on components of the reusable pen base which rotate at different times during dose setting and injecting use of injection pen 440. To facilitate the signal communication between controller 426 and such a rotating sensor array, a slider assembly is disposed therebetween. As diagrammatically shown in FIG. 22, an array of sensor contacts 546'-551' are installed on a partially shown first pen component 558 coaxially mounted on a partially shown second pen component 559. Pen component 558 is completely ringed by six electrically conductive, metal bands 560-565 that fit within channels in its outer radial periphery. Bands 560-565 are in contact with the outward ends of sensor contacts 546'-551', respectively, that extend through the radial thickness of component 558. Sensor contacts 546'-551' are similarly structured and arranged to the sensor contacts of the embodiment of FIGS. 19-21, and contact a not shown rotational matrix, similar to matrix 500, that encircles pen component 559. Slider assembly 570 includes six resilient electrical contacts 571-576 having free ends which slide along bands 560-565 as pen component 558 rotates, and such sliding contact results in an electrical connection between sensors 546'-551' and slider contacts 571-576 at any rotational position of pen component 558 relative to slider assembly 570.

If the internal workings of the injection pen are configured such that pen components 558 and 559 do not translate or move axially during operation, slider assembly 570 may be mounted to a stationary pen base component, such as a microprocessor containing flexible circuit board fixed to the injection pen housing and which serves as controller 426. Slider contacts 571-576 are connected to circuits on this circuit board routed to the controller microprocessor. For this type of slider assembly mounting, other than limited axial play as may be required for the working parts of the injection pen, slider assembly 570 is axially and rotationally fixed within pen base 444. If pen components 558 and 559 translate together during pen operation, slider contacts 571-576 are wired to controller 426 and slider assembly 570 is keyed to, for example, the pen outer housing and connected to pen component 558 so as to translate with but not rotate with the array of sensor contacts 546'-551'.

The injection pen controller 426 that processes signals from the sensor contacts of the automatic container recognizer 422 and doseable quantity identifier 424 to determine display information may be constructed and installed within pen base 444 in any suitable fashion known in the art. In one embodiment of the invention, controller 426 includes a battery-powered, programmable microcontroller mounted on a main printed flexible circuit board that is generally U-shape and flexible so as to conform to the interior of the pen base housing and to provide a hollow in which extend the internal working parts of pen base 444. The flexible circuit board is connected to the housing with locating pins and adhesive. In an alternate embodiment, an application specific integrated circuit or ASIC may be substituted for the microprocessor.

Injection pen display 428 is operatively coupled to the microcontroller 426 and is visible through a transparent housing window of pen base 444. Display 428, such as a liquid crystal display, visibly displays to a user information useful to the operation of the injection pen. For example, as best shown in FIG. 13, display 428 is caused by microcontroller 426 to display at 580 information about the medicine within the held cartridge as recognized by automatic cartridge recognizer 422, at 582 the amount of therapeutic the injection pen stands ready to administer upon the operation of the injecting mechanism of pen 440 as described further below, and at 584 the remaining strength of the battery that powers the electronic components of injection pen 440. The information shown at 580 relates to the concentration of the medicine, as explained further above, but other types of information may be provided. The units of the dose to be administered is shown in FIG. 13 as being imprinted on the underside of the housing window at 586, but may be part of the display controlled by microcontroller 426.

The design of the therapeutic dose indicating apparatus in injection pen 440 will be further understood in view of the following explanation of its operation. While cartridge assembly 442 is mounted to pen base 444, controller 426 remains in a ready state with all of the display elements turned off so as to not display any information to a user. In this ready state, controller 426 processes signals received from the sensor contacts of automatic cartridge recognizer 422 to identify, for example, the concentration of the medicine contained within the cartridge assembly as represented by the identifier band. In this ready state, controller 426 also processes signals received from the sensor contacts of closeable quantity identifier 424 to identify the position of matrix 500 relative to sensor array 502.

Controller 426 advances from the ready state into the operational state, and display 428 is thereby activated, when controller 426 senses further user action on pen 440. For example, such action sensing will typically be a recognition that matrix 500 is being moved relative to sensor array 502 during manipulation by the user of the dose setting mechanism. Other action which may be sensed is operation of a not shown on/off button which may be located on pen base 444, or as part of knob 508 of the injecting mechanism.

When advanced to the operational state, controller 426 causes the concentration identified with automatic cartridge recognizer 422 to be displayed at 580. If controller 426 fails to recognize any concentration information, an error message such as "--," or no message at all, is displayed at 580 instead of any numerical concentration value. Recognition failure may result from a cartridge assembly being entirely absent from, or not properly mounted to, pen base 444, or from a cartridge identifier being damaged or absent from the assembly, or from an internal failure in the automatic cartridge recognizer circuit. When concentration information is not automatically recognized, the concentration used by controller 426 may be user configurable. For example, set button 588 shown in FIG. 13 is circuited with controller 426 and is depressable to select, and have displayed at 580, any of the standard concentration values, such as 6, 12 and 24 mgs in the case of hGH, preprogrammed into controller 426.

While controller 426 is in the operational state, as knob 508 is rotated by a user to set the dose to be delivered, controller 426 continually receives input in real time from the sensor contacts of doseable quantity identifier 424 to identify the position of matrix 500 relative to sensor array 502. Controller 426 processes the input to determine to which position the dial 506, and therefore matrix 500 in the shown embodiment, has been rotated from the "zero" dial position at which no volume of medicine will be delivered if the injecting mechanism of the pen is operated. For example, if the "zero" dial rotational position is when sensor 546 engages column 516, controller 426 recognizes when sensor 546 is in engagement with each of columns 517-539 to determine which percentage of a dial revolution has been made. Typically, automatically during, or manually after, injection of the set dose the dial is returned to its original "zero" position for subsequent use. However, controller 426 may be designed to determine dose setting based on any starting point of the dial.

Controller 426 senses the rotational position of the dose setting dial via the matrix/sensor array interface whether the dial is being rotated, or dialed up, so as to increase the set dose, or being dialed down to decrease the set dose. In addition, controller 426 is programmed to account for one or more complete dial revolutions during dose setting. During dose setting, by recognizing the matrix position relative to the sensor array at the orientation from which the dial is being rotated, controller 426 recognizes in which direction the dial is being rotated during movement to the "zero" dial rotational position. Specifically, if the "zero" dial rotational position is when sensor 546 engages column 516, controller 426 recognizes that the set dose is being increased if sensor 546 reaches column 516 immediately after being in column 539, and that the set dose is being decreased if sensor 546 reaches column 516 immediately after being in column 517.

For example, with the dial initially arranged in the "zero" dial rotational position, during dialing up when that "zero" dial rotational position is reached for the first time and the dialing up continues, and then the "zero" dial rotational position is reached for the second time and the dialing up continues, when controller 426 senses via the matrix/sensor array that, for example, dial rotation is halted by a user when the dial reaches the sixth rotational position from the "zero" position, controller 426 recognizes that a fifty-four unit volume dose has been set for injection (i.e. two complete revolutions each of twenty-four positions or unit volumes in the shown embodiment plus the six additional positions). If a dose is initially set at too large an amount by a user who then reduces that dose setting before injecting, dialing down through the "zero" rotational position attained at one or more complete dial revolutions will be accounted for by controller 426.

The dose volume that controller 426 identifies with doseable quantity identifier 424 is used to display the actual therapeutic amount to be injected. Specifically, controller 426 essentially multiplies the concentration displayed at 580 by the volume set by rotation of dial 506 and causes the injectable amount of therapeutic to be displayed at 582. The multiplication step described above is normally performed by controller 426 referencing a look-up table populated with data based on therapeutic concentration and the number of dial "clicks" selected. The display at 582 displays the injectable amount at all times throughout the dose setting process. For example, when each "click" corresponds to a unit dose volume of 0.024 milliliters, when the cartridge concentration is 6 mg as explained above, each dialing up of dial 506 in an amount of 15 degrees, or one click, causes display 582 to be increased by 0.05 for the shown milligram labeling, and similarly when the cartridge concentration is 24 mg, each one click dialing up of dial 506 causes display 582 to be increased by 0.20 for the shown milligram labeling. Thus, at all times the amount of therapeutic displayed at 582 is the medically significant amount actually injectable by operation of injection pen 440. No calculations based on the concentration of hGH loaded in the cartridge assembly 442 need be made by the user to figure out how much hGH is being injected.

In addition, the display amount at 582 also works throughout injection (i.e., displays the quantity still to be injected) if the pen components on which the matrix and sensor array are disposed are designed to appropriately rotate relative to each other during injection.

After injection pen 440 is used to inject the set dose, such as by axially pressing on knob 508 and moving dial 506 back into pen base 444, controller 426 automatically returns to an off state, and the display elements of display 428 all turn off, following a certain time period of inactivity. In the event after dose setting no injection is immediately made, the display remains on until the injection is made, after which the pen turns off after the above-described inactivity.

As further described below, the doseable quantity indicator may be used in delivery devices that lack the automatic cartridge recognition system described herein, such as in devices in which different medicines each having only a single concentration are being delivered. In such devices, the display at 582 can be a numerical value or another piece of information representative of the actual doseable volume.

Figure 23:
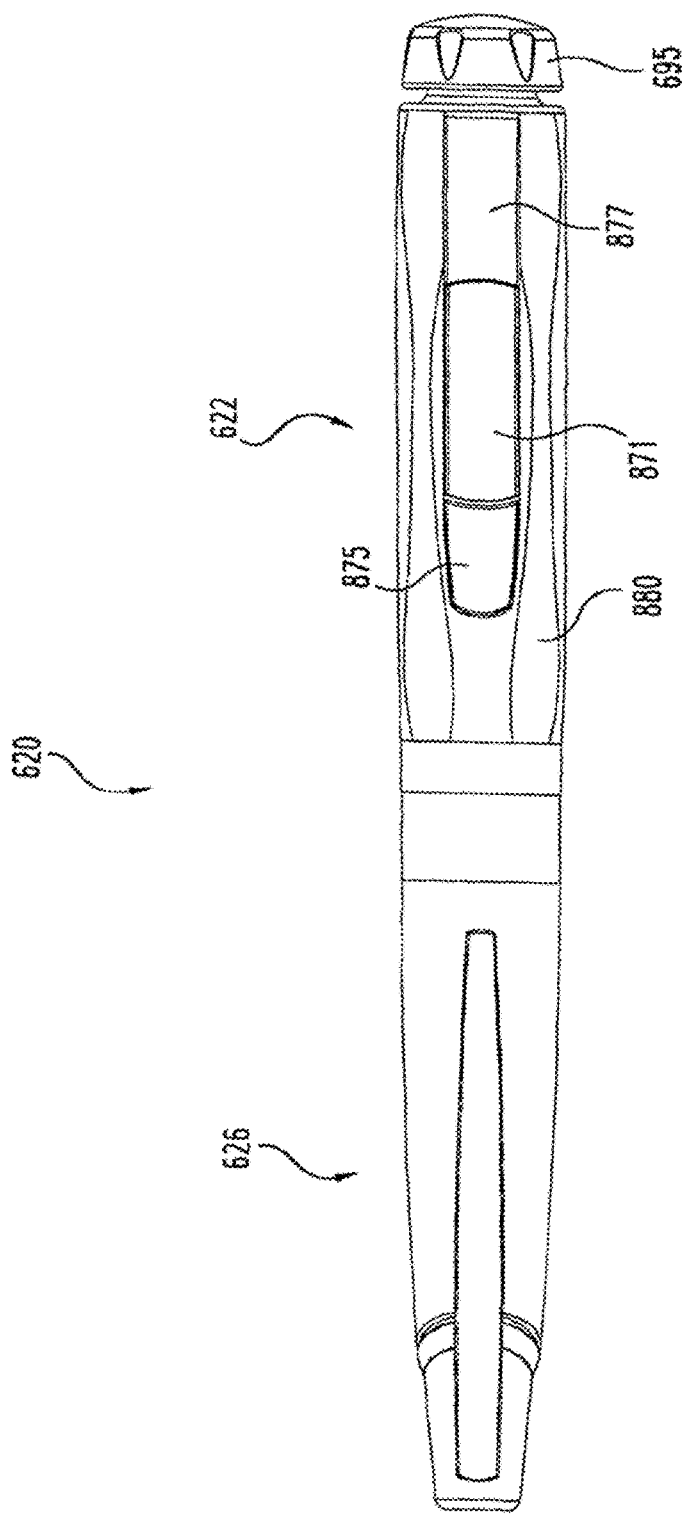
FIG. 23 is a top view of one form of an injection pen of the present invention equipped with an assembly for selectively rotating a drive sleeve to inject a set dose.

Referring now to FIG. 23, there is shown an exemplary embodiment of a medication injector apparatus with an assembly for selectively rotating a drive sleeve of the present invention. The apparatus, generally designated 620, is shown in the form of a reusable injection pen, although other forms of portable injectors are within the scope of the invention.

Figure 24:
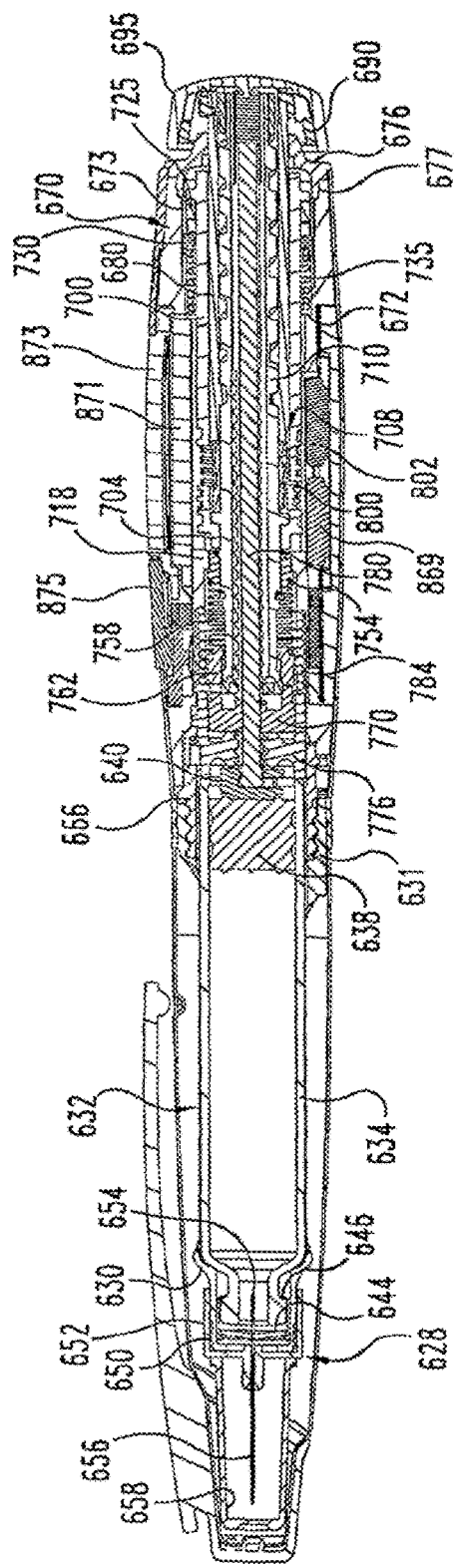
FIG. 24 is a cross-sectional front view of the injection pen of FIG. 23 prior to the dose setting knob being manually rotated out to set the dose to be delivered by further operation of the injection pen.
Figure 25:
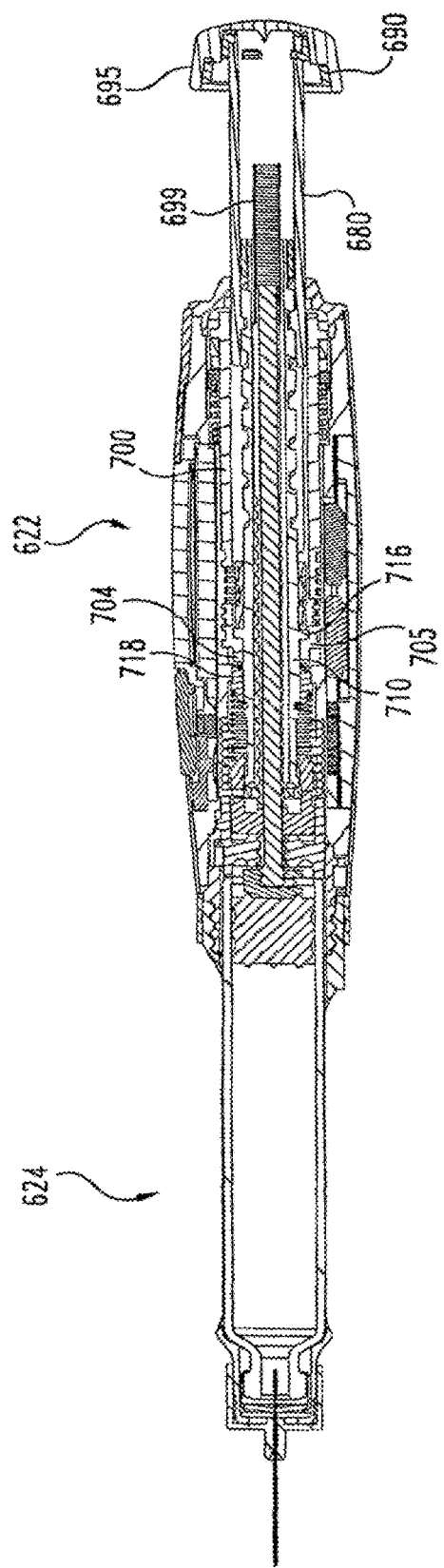
FIG. 25 is a cross-sectional view conceptually similar to the view of FIG. 24 after the cap has been removed, the pen is in a primed state, and the dose setting knob has been rotated out to set the dose for delivery.

Injection pen 620 includes a reusable pen base, generally designated 622, to which is attached a cartridge assembly generally designated 624 and further referenced in FIG. 25. In FIG. 23, the cartridge assembly is shown substantially encased within a removable cap assembly 626. As further shown in FIG. 27, cap assembly 626 comprises a metal tip clip 627 swaged to metal cap shell 629, and a plastic tubular cap insert 633 that is secured within shell 629 and includes modules for attachment to the cartridge holder. Insert 633 is not shown in FIG. 24 to facilitate illustration. Pen base 622 houses a dose setting and injecting assembly that when operated causes a quantity of medicine to be selected and then expelled from cartridge assembly 624 through pen needle assembly 628 further referenced in FIG. 24.

With additional reference to FIGS. 24-27, cartridge assembly 624 is of a general type known in the art and includes a reusable cartridge holder or retainer 630. The proximal end 631 of holder 630 is connectable in a suitable fashion, such as via an internal threading, to the distal end of pen base 622. Holder 630 defines a chamber into which a disposable cartridge 632 is loaded for use.

Cartridge 632 is of a standard design generally described above and includes a medication-filled glass housing 634, piston 638, septum 644 and cap 646. A foot 640 that is rotatably secured via a one time snap-fit on the distal end of a drive screw 780 extendable from pen base 622 distributes moving force on piston 638. Openings or windows 642 on opposite sides of cartridge holder 630 allow visual observation of the quantity of medicine remaining within the held cartridge. External threads 650 on the distal end of cartridge holder 630 allow mounting of hub portion 652 of pen needle assembly 628. When assembly 628 is mounted as shown in FIG. 24, the proximal end 654 of needle cannula 656 held in hub portion 652 pierces septum 644, and medicine is expelled from cartridge 632 through needle cannula 656 during injecting use of pen 620. Although the needle assembly is shown as having a single injection needle, needle assemblies which may be used with pen 620 may be of various pen types known in the art, including, but not limited to, assemblies with one or more shortened injection needles, including microneedle arrays.

In the shown embodiment, pen needle assembly 628 further includes a needle cover 658 which has an interference fit to hub portion 652. Cap assembly 626 fits over the distal end of cartridge assembly 624 when pen 620 is not being used, and is removably snap fit to cartridge holder 630 using mating detents and indents. A camming feature on cartridge holder 630 serves to rotationally align cap assembly 626 properly on cartridge holder 630 when being connected together, and further pushes cap assembly 626 axially away from the cartridge holder 630 to disengage any snap fit therebetween when the cap assembly is rotated relative to the cartridge holder during its removal therefrom. A decorative trim ring 662 is fixedly connected, such as via adhesives, around proximal end 631 of cartridge holder 630 for aesthetic purposes.

In pen 620, after the contents of a given cartridge 632 are exhausted by use of the injection device, a user disconnects holder 630 from the pen base 622, removes and disposes of the spent cartridge 632, and then inserts a replacement, disposable cartridge into the reusable holder which is then reconnected to pen base 622 for use. Windows 642 help in gripping the cartridge during the removal of the cartridge from holder 630.

In an alternate embodiment not shown, and rather than the separable cartridge and holder shown, the cartridge assembly may be differently configured as is known in the art, and such as described above. For example, the cartridge assembly 624 may be assembled from component parts during production into a disposable unit handled by a user as a single piece.

Cartridge holder 630 is removably mounted to pen base 622 by screwing its internally threaded proximal end onto the external threading 664 of a tubular front housing 666. Front housing 666 is snap fit via angularly spaced detents 667 to a distal end of a housing main body, generally designated 670. Angularly spaced keys 668 of front housing 666 fit within keyways 671 of housing main body 670 to prevent relative rotation therebetween.

The housing main body 670 is molded in one piece, but a multiple piece assembly may be employed. Housing end cap 676 is snap fit via its protruding collar 677 to the proximal end of main body 670 to be axially fixed together.

Proximally extending beyond and axially shiftable through the central opening of end cap 676 is a cylindrical sleeve-shaped dial 680. A set of three angularly spaced notches or keyways 681 located along the proximal edge of dial 680, and a set of three snap slot recesses 682 in the dial, respectively accommodate keys 692 and latching ribs 693 of a base 690 of a dial assembly to provide a rigid, permanent assembly of dial knob base 690 with dial 680 via a one-time snap fit. The dose knob assembly includes a cover 695 that is fixed to base 690 with adhesive, and with keys 696 of cover 695 fitting in notches 694 of base 690. In one embodiment, dose knob base 690 is plastic and cover 695 is a die-cast component. Gripping features 697 formed in the exterior periphery of cover 695 enhance gripping of the dial knob assembly during its rotating or dialing to set the dose. Within its interior, dial knob cover 695 includes a centering protrusion, or alternately a ring-shaped seat, which centers the distal end of priming spring 699.

Adjacent its distal end, dial 680 includes a pair of radially protruding keys 683 which insert within longitudinally extending keyways (not shown) formed in the interior surface of barrel 700. This keying provides consistent rotational movement between dial 680 and barrel 700 while permitting dial 680 to move axially relative to barrel 700. A double start helical threading 685 radially inwardly protruding from the cylindrical interior surface of dial 680 mates or screws into helical grooves 712 formed in the exterior surface of a drive sleeve 710 of a drive sleeve assembly, generally designated 708. By making one of the double start threads 685 and its corresponding groove 712 thinner than the other thread and groove, a one way assembly of the dial to the drive sleeve is achieved. Different thread configurations, including a single thread and groove connection, may be used in alternate embodiments. An arrowhead 686 formed on dial 680 shows the direction dial 680 is inserted onto drive sleeve 710 to facilitate assembly. Zero stop 713 is the distal end of grooves 712 which is abutted by dial threading 685 to prevent the dial 680 from being dialed below a zero setting of the pen. A maximum dose stop, formed of a collar 720 with a pair of axially extending latching prongs 721 that snap fit into recesses 714 in drive sleeve 710, fits around the proximal end of drive sleeve 710 to engage dial threading 685 at the proximal end of grooves 712 to prevent the dial 680 from being dialed above a maximum setting.

Barrel 700 is formed with an annular rib 702 at its proximal end that extends continuously around the outer circumference of the barrel. The distal face of barrel rib 702 includes a series of axially extending, unidirectional teeth 703 for engagement with an annular dial clicker 725. The proximal face of dial clicker 725 includes a ring of axially extending, unidirectional teeth 726 that mate with barrel teeth 703. The distal face of dial clicker 725 includes a ring of axially extending, unidirectional teeth 728 that mate with axially extending, unidirectional teeth 732 on the proximal face of an annular dial clutch 730.

A set of four keys 733 protrude radially outwardly from the external periphery of clutch 730 and slidably fit within axially extending keyways 673 in housing main body 670 to prevent rotation of clutch 730 relative to the housing. A helical compression spring 735 having one end abutting a bulkhead 672 formed in housing main body 670 and the other end seated on the distal face of dial clutch 730 biases clutch 730 into clicker 725 into barrel rib 702 to provide audible clicks during dose dialing and to provide rotational positioning during dialing. In particular, when dial 680 is dialed up so as to axially move proximally, clicker teeth 728 slide past clutch teeth 732 as the meshing of clicker teeth 726 with the teeth 703 of the rotating barrel 700 causes rotation of clicker 725. When dial 680 is dialed down, the barrel teeth 703 slide past clicker teeth 726 as clicker 725 is rotatably fixed by the meshing of clicker teeth 728 with teeth 732 of the rotatably fixed clutch 730. As is known in the art, this sliding motion of the teeth produces the dial clicks.

Barrel spring 735 biases barrel 700 proximally such that except during injecting operation of pen 620 as described below, the axially extending external splines 704 at the barrel distal end do not mesh with complementarily internal splines of bulkhead 718 formed in housing main body 670. The splines of bulkhead 718 are twenty-four in number and equally angularly spaced circumferentially around the drive sleeve. The proximal retraction of barrel 700 is halted when the proximal face of barrel lip 705 abuts drive sleeve flange 716 and the drive sleeve has been retracted proximally until ring 760 has pressed clicker 754 into full engagement with splines of the housing bulkhead 718. Splines 704 are integrally formed on inward lip 705 of the barrel in four arcuate segments, the spacing between segments providing clearance for lugs 655. The proximal face of lip 705 also serves as a contact face for injection force that is placed on drive sleeve 710, as well as a bearing surface for the relative rotational movement of drive sleeve 710 and barrel 700.

When barrel 700 is shifted distally so as to compress barrel spring 735 during injecting, barrel splines 704 mesh with internal splines of bulkhead 718 to prevent rotation of barrel 700 relative to housing 670. In an alternate embodiment, the prevention of rotation of barrel 700 relative to housing 670 may be accomplished with interfacing, unidirectional teeth.

The distal region of drive sleeve 710 is generally cylindrical, although shown with slight facets for improving manufacturability, and includes circumferential groove 748, diametrically opposed recesses 750 and diametrically opposed longitudinal slots 746. Injection clicker 754 is rotatably fixed with drive sleeve 710 by four 90° spaced apart lugs 655 integrally formed with the drive sleeve which fit into four corresponding recesses 647 in the proximal face of clicker 754. Clicker 754 is biased in the proximal direction by clutch spring 758. Retainer ring 760 fits in groove 748 and prevents disassembly of the clicker from the drive sleeve. When drive sleeve 710 is biased proximally by operation of barrel spring 735, lugs 655 engage the splines of bulkhead 718 and prevent rotation of drive sleeve 710. When the biasing of barrel spring 735 is overcome and the drive sleeve is shifted distally during injecting, lugs 655 are shifted away from bulkhead 718 to allow lugs 655 to disengage from splines of bulkhead 718, thereby allowing the drive sleeve 710 to rotate. Clicker 654 is allowed to move axially with respect to the drive sleeve allowing clicker teeth 656 to slide over the ramped end faces of the splines of bulkhead 718 when drive sleeve 710 is rotated to create an audible clicking indication of operation and to provide a rotational positioning during injection. The distal end of clutch spring 758 abuts the proximal face of an injection clutch 762 that is rotatably fixed with drive sleeve 700 by keys 764 that slide within slots 746. Clutch 762 is further snap fit within recesses 750 so as to have a limited axial play on drive sleeve 710 to accommodate the axial motion of the drive sleeve during injecting, and axial travel of the floating nut 776 during installation of the cartridge assembly 624. The distal face of clutch 762 includes a ring of torque transmitting teeth 766.

Clutch teeth 766 selectively mate with teeth 772 of a drive clutch 770 axially retained within injection nut 776. Internal keys 774 of clutch 770 slide within two longitudinal keyways or slots in threaded drive screw 780 and cause the drive screw to be rotated with the clutch. The drive screw keyways or slots are formed by corner or right-triangular shaped cuts in the screw along its length, which cuts are generally on opposite sides of the screw. The lead edge of the first corner cut is radially aligned in the screw, as well as diametrically aligned with the lead edge of the second corner cut, resulting in the non-aligned or trail edges of the first and second corner cuts being parallel. Drive screw 780, which extends within an axial bore through drive sleeve 710, threadedly engages an internally threaded bore within injection nut 776. Nut 776 is rotatably fixed but axially movable within housing 670 via angularly spaced keys 777 that slide within axially aligned recesses 674 in housing main body 770. When drive screw 780 is caused to be rotated by the forced rotation of drive clutch 770, the drive screw advances in the distal direction as it screws through nut 776. Priming spring 699 press fits onto the proximal end of drive screw 780. During cartridge replacement, when screw 780 is driven back when being reset during mounting of a replacement cartridge-filled cartridge assembly 624 to pen base 622, spring 699 is compressed upon contacting the dial knob cover 695 to bias the drive screw forward toward cartridge piston 638. Injection nut 776 is biased in the distal direction by an injection spring 784 that acts between a housing bulkhead and the proximal face of nut 776, which biasing is overcome by engagement with the distal end of cartridge 632 during mounting of cartridge assembly 624.

In the embodiment shown, electronics are used in determining and displaying the dose that is set and remaining to be injected during subsequent use of pen 620. Therefore, in the shown embodiment, dial 680 need not be furnished with any numbers or other markings that provide a user with a visual indication as to what quantity of medicine the pen has been manipulated to inject upon use, and the dial thus serves as an extension of the grippable knob. The electronics include an electrically conductive matrix pattern 800 around a plastic sleeve 802 that is fixed, through a method such as adhesive bonding, a snap fit or press fit, to drive sleeve 710. A not shown; axially extending key of sleeve 802 fits within an opening in annular flange 716 of drive sleeve 710 to prevent relative rotation, and allows for a proper orientation of the matrix 800 relative to drive sleeve 710. Flange 716 also provides a bearing surface for the relative motion between drive sleeve 710 and barrel 700, takes the distal axial load of injection, as well as takes the proximal axial load of retraction, by spring 735. The matrix-including sleeve 802 together with drive sleeve 710 form the drive sleeve assembly 708 that rotates and translates as a single unit during operation.

Matrix sleeve 802 is electrically contacted by contact ends of a pair of insert molded leaf spring contact assemblies, generally designated 805 and 806, further shown in FIG. 29. Contact assembly 805 includes a plastic base 807 that inserts within the cross portion of a T-shaped opening 808 in barrel 700. A wedge shaped periphery of base 807 prevents over insertion. Four metal leaf springs 810, 811, 812 and 813 are captured in base 807. The matrix contact ends 810a, 811a, 812a and 813a of leaf springs 810-813 extend through the base of opening 808 and brush against the matrix sleeve to make electrical contact with the conductive pattern 800. Wire contact ends 810b, 811b, 812b and 813b of leaf springs 810-813 extend external to barrel 700 and fit within the four most proximal circumferential grooves 706 of a set of six such grooves in the exterior of barrel 700 which accommodate contact rings.

Contact assembly 806 is similarly constructed to contact assembly 805 with a plastic base 814 holding three metal leaf springs 816, 817 and 818 including matrix contact ends 816a, 817a and 818a, and wire contact ends 816b, 817b and 818b. Plastic base 814 inserts within a not shown barrel opening that is longitudinally and angularly offset from barrel opening 808. Wire contact ends 816b, 817b and 818b extend external to barrel 700 and fit within the three most distal circumferential grooves 706 of the set of six such grooves. By placing contacts 813 and 816 at the same longitudinal position and in the same groove 706, a redundant contact for grounding the matrix pattern is provided. In the shown embodiment, matrix contact ends 816a, 817a and 818a are angularly offset 180 degrees from matrix contact ends 810a, 811a, 812a and 813a, but other spacings may be employed.

With reference again to FIG. 27, encircling barrel 700 are six contact rings made of metal wraps or coiled springs 820-825. Rings 820-825 seat within the six axially spaced, circumferential grooves 706 in the exterior of barrel 700, as well as grooves 809 formed in base 807 and grooves 815 of base 814, and are in electrical contact with wire contact ends 810b, 811b, 812b, 813b and 816b, 817b and 818b, respectively. Rings 820-825 allow contacts of a rotationally stationary slider assembly 838 to remain in contact with the rings regardless of the relative rotational positions of the rings.

Figure 30:
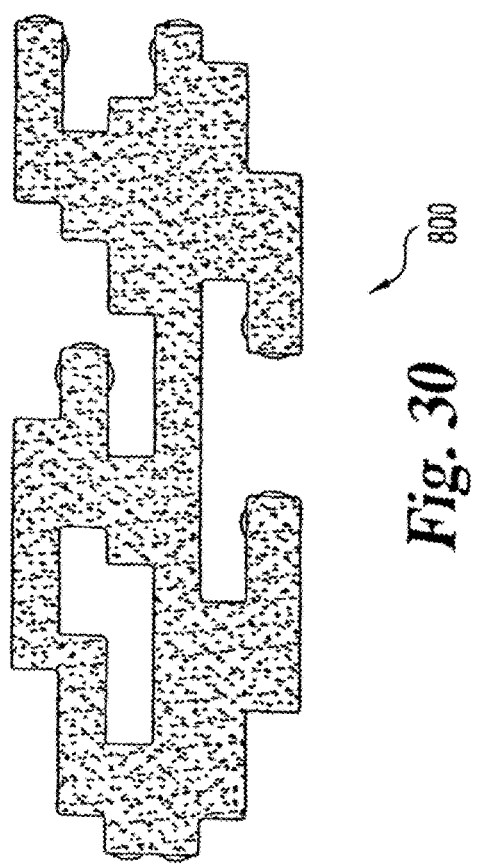
FIG. 30 is a plan view of the rotational matrix of FIG. 27 shown unwrapped and removed from the rest of the injection pen.

Matrix 800 is designed and constructed conceptually similar to matrix 500, but is adapted to work with the angular positionings of matrix contact ends 810a, 811a, 812a, 813a, 816a, 817a and 818a such that twenty-four different angular orientations of barrel 700 relative to drive assembly 710 can be recognized. One suitable matrix 800 is shown two-dimensionally in FIG. 30. The rounded protrusions shown on the matrix in FIG. 30 are not part of the effective pattern, but rather are used to help hold the pattern in the part into which it is insert molded. Still further, the pattern of matrix 800 is designed so that single-point errors in contacts related to matrix data associated with the contact ends 810a, 811a, 812a, 817a and 818a, and not the ground contact ends 813a and 816a, that are different than the change expected by moving from one matrix position to an adjacent matrix position in either direction are readily detected by controller 867 for the purpose of detecting errors in the pen operation at all times the pen is on. Specifically, the matrix 800 is designed such that during relative rotational motion of the pen components which moves the matrix one position from its current position (e.g., a movement of 15° for the twenty-four column matrix shown), the change of one of the signals associated with matrix contacts ends other than contacts 813a and 816a results in only one of the following: (a) a shift to the code corresponding to an adjacent position, (b) a shift to a code corresponding to none of the twenty-four positions, or (c) a shift to a code corresponding to a position outside of a given range, such as a range from two to six positions inclusively away from the current position. Other ranges, from two to three or four or five positions, or two to eight or more positions, may alternative be employed. In other words, for any of the twenty-four rotational positions, the code of the matrix data within the range of two to six positions away from a given position in either direction differs by at least two data points from the given position. Thus, during pen use, whether during manual dialing up a dose, or manual dialing down a dose, or during medicine injecting, if the controller receives information suggesting a movement of greater than six rotational positions from the previously recognized position, which such movement is considered by the pen to be too large a movement and therefore an error, unless within a short period of time set by the manufacturer, such as the time between display updates, during which time the controller continues to check the matrix data, the received information is back within the accepted range of positions from the previously recognized position, the controller causes an error message to be displayed. If the received information does return to the accepted range within the set period, the pen controller recognizes the erroneous reading as being an aberration and ignores it as such, and does not display an error message or require a resetting of the pen.

It will be recognized that one skilled in the art, in view of the teachings herein, can provide other ways for controller 867 to determine the validity of a sensed position code, based upon a previously recognized position code. For example, it is not necessary for the matrix 800 to provide unique patterns for all twenty-four positions of a revolution, but only for those positions within a valid range, such as one to six positions, on either side of any given position. The controller would compare a sensed position code to the position codes within the range adjacent the previous code to determine around which of the non-unique position codes was being sensed. The foregoing approach would allow the twenty-four positions to be captured through a five-row matrix, which is a four-bit signal, instead of the shown six-row matrix 800, which is a five-bit signal. The reduction to a five-row matrix is not required, but could be used to reduce the number of parts or decrease device length. If a five-bit signal were still to be used, such may improve the overall reliability of the device without increasing device length because redundancy may be added.

Still further, a matrix 800 could be created where matrix data associated with two matrix contact ends other than contact ends 813*a* and 816*a* change when shifting one column of the matrix 800, instead of only one data point as described directly above. Such an approach would allow controller 867 to reject all single-point error of such sensor contacts instead of only those that would result in a change of more than one data point, thereby improving the reliability of the device. For such a two-bit shift, if twenty-four unique rotational positions are desired, a seven-row matrix pattern, as opposed to the six-row pattern shown, will be required.

Figure 28:
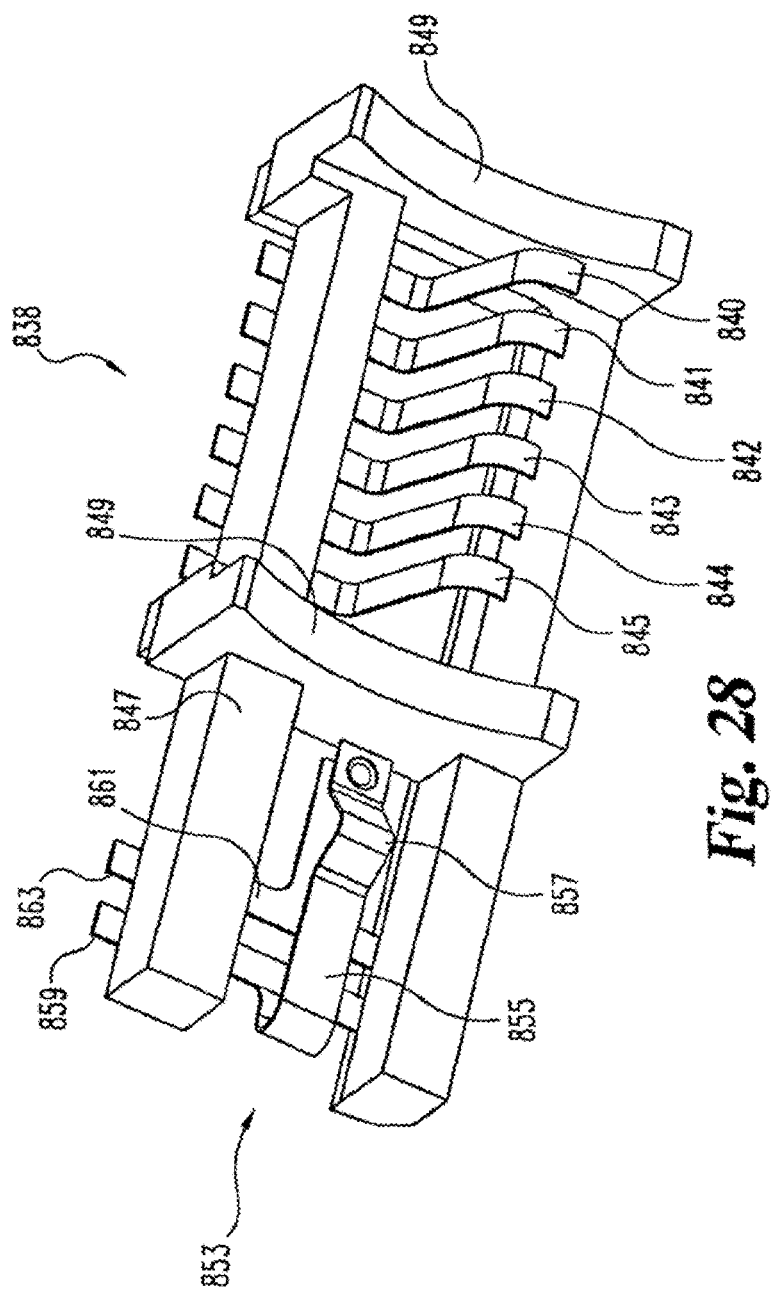
FIG. 28 is a front perspective view of the slider assembly of FIG. 27.

Each of contact rings 820-825 is directly engaged by one of six sliding contacts 840-845 of a slider assembly, generally designated 838, shown further in FIG. 28. Sliding contacts 840-845 are made of metal in a leaf spring form and are mounted on a plastic chassis 847 between a pair of keys 849 that radially project from the chassis. Keys 849 insert within a pair of circumferential grooves or keyways 707 in barrel 700 that flank on either axial side the set of six grooves 706. The fitting of keys 849 within grooves 707 causes slider assembly 838 to move axially with barrel 700, but allows barrel 700 to be rotated relative to slider assembly 838, all the while with sliding contacts 840-845 in electrical communication with contact rings 820-825.

Slider assembly 838 is fixedly connected to a flexible circuit board 865 such that the contacts can transmit to the microcontroller via the circuit board 865 the sensed matrix pattern. Slider assembly 838 is positioned on the board during manufacture via a pair of nubs that project from the back of chassis 847 and fit within notches 851 in the board. Slider assembly chassis 847 fits within opening 678 of housing main body 670, which opening serves as a keyway in which slider assembly 838 is axially movable but rotatably fixed relative to the housing.

To accomplish sensing of relative motion of barrel 700 and drive sleeve assembly 708, the matrix 800 on sleeve 802 provides a selective conductive path between the six contact rings 820-825. Contact ring 823 is always grounded, and that grounded ring, via its associated matrix contact ends 813*a* and 816*a*, is always in contact with and thereby grounds the conductive matrix 800, except at the home rotational position when none of the other rings 820, 821, 822, 824 and 825 via their associated matrix contact ends is in contact with the matrix pattern 800. The matrix pattern 800 selectively shorts the current across the appropriate rings to form a code that is then picked up by slider contacts 840-845 and sent to the microcontroller for recognition.

Although described above as the matrix being grounded, in other embodiments, the matrix could be activated not by a ground signal, but rather by any voltage that is distinctly recognizable by the controller. For example, for a controller where the only options are logic high and ground, rather than the ground signal described above as being the activating signal, a logic high signal of approximately three volts may be used to activate the matrix.

Slider assembly 838 also includes an injection switch, generally designated 853. Switch 853 has a resilient contact 855 made of metal in a leaf spring form and with a ramped region 857. When barrel 700, and thereby slider assembly 838, are moved axially a short distance during a first phase of injecting operation, ramped region 857 is pressed radially outward by contact with housing surface 679 such that resilient contact 855 completes a circuit with fixed contact 861 of the injection switch. Resilient contact 855 includes a contact end 859, and fixed contact 861 includes a contact end 863, that are each electrically connected to circuit board 865 to convey electrical signals to the microcontroller. During this slider assembly axial movement, the portion of flexible circuit board 865 to which the slider assembly is mounted also moves axially relative to the remainder of the board. The closing of injection switch 853 is recognized by microcontroller 867 as the start of the injecting operation of the pen, rather than the pen being dialed down or up in preparation for injecting.

Flexible circuit board 865 is a two-layer flexible circuit board that wraps around the housing main body 670 and is connected to main body 670 with locating pins and adhesive. Flexible circuit board 865 serves as the base to which are mounted microcontroller 867, which is programmed to control the electronic operations of pen 620, batteries 869 for powering the electronics, and an LCD display 871.

The electronics of pen 620 are capable of sensing the relative rotational motion of the drive sleeve assembly 708 within the barrel 700, which barrel and drive sleeve assembly are maintained in a consistent axial position with respect to each other. During dose setting, barrel 700 rotates while drive sleeve assembly 708 is rotationally fixed within the housing, and during dose injecting the barrel is rotationally fixed and the drive sleeve assembly rotates within the housing.

A clear plastic lens 873 is adhered to housing main body 670, and protectively covers display 871 and provides magnification of the display readout. Push button 875 used in controlling the pen electronics is pivotally mounted to lens 873 and interfaces with a switch actuator 874 that activates a snap dome switch that is electrically connected to circuit board 865. The microcontroller 867 is programmed to turn on the display for operation when button 875 is manually depressed. In one embodiment, button 875 can be used to change data stored in memory, or a setting of a clock associated with the microprocessor. For example, data stored in memory associated with the microprocessor, such as the date, is adjustable by first pressing and holding button 875 for a set period, such as three seconds, to transition the pen into an adjust mode, and then by axially pressing on the dial knob assembly to move slider assembly 838 and activate injection switch 853 to increment the data being changed. A bezel 877 adhered to housing main body 670 serves as a decorative trim piece and along with lens 873 and push button 875 is exposed through a window 879 of an outer skin 880 formed from metal and which is adhered to housing main body 670.

A seal 882 made of foam is captured between the underside of lens 873 and an upper surface of the flexible circuit board 865. Seal 882 resists any fluid that may be present on the pen exterior along the interconnection of the push button 875 and lens 873 from reaching the internal electronics of pen 620. A frame filler 885, which is provided to facilitate pen assembly and fits within notches in housing main body 670, serves as an additional base on which display 871 is adhered, and is an additional bonding surface for skin 880.

A cover portion 887 is adhered to the underside of housing main body 670; and has internal relief to allow room for the electronics. A metal outer skin 880 is adhesively mounted to both housing main body 670 and cover portion 887 to provide an attractive appearance to pen 620.

The structure of injection pen 620 will be further understood in view of the following explanation of its operation. When the user needs to inject herself with a dose of the medication, pen 620 first is turned on by depressing button 875, which causes display 871 to display the current date and time according to the pen's internal clock, and a "0" as to the amount of medicine the pen is prepared to deliver. Pen 620 also may be turned on by beginning to rotate the dial knob assembly, or alternatively by pressing the dial knob assembly to trigger the injection switch. If after the pen is turned on via button 875 or by pressing the dial knob assembly, the dial knob assembly is axially pushed distally such that injection switch 853 is activated, the date, time and amount of the last injection is caused to be displayed. If the memory of pen 620 is adapted for multiple dose memory, each additional distal plunging of the dial knob assembly will cause the then previous injection date time and amount to be displayed, so that the user can cycle through the stored previous doses, which may be ten or more doses. To exit the dose memory mode, the user can wait for a set period of time, such as eight seconds, without dialing the dose knob or pressing any buttons, or by dialing the dose knob from the "0" position, or by pressing and releasing the dose knob a sufficient number of times to cycle through the entire multiple dose memory.

Pen 620 is then manipulated such that the user selects the dose to be administered. The following explanation will assume pen 620 has already been primed as is suggested, which priming step merely involves operating the pen in the manner described below to discharge a small dose to expel any air from the cartridge. In a pen having multiple dose memory, an indication that such dose was a priming dose can be tagged in memory, such as by pressing and releasing mode button 875 immediately following the prime delivery so long as the microprocessor 867 senses the injection switch 853 is no longer activated, such as prior to the completion of a five-second post injection timer. When a user reviews the doses in memory, a priming dose may be indicated by that dose alternating over time with a "P" in the display. The prime tag alternatively may involve a press and release of mode button 875 by the user upon reaching a prime dose when reviewing the doses stored in the dose memory.

To select the dose, the user grips the cover 695 of the dial knob assembly between typically a thumb and forefinger and begins to rotate it relative to the rest of pen base 622. This rotation causes corresponding rotation of dial 680, and further barrel 700 rotates simultaneously due to its keying with the dial. As dial 680 and the dial knob assembly rotate, they also axially translate in the proximal direction as dial 680 screws up drive sleeve 710 due to its threaded engagement therewith. As the dial screws out, it proximally extends farther beyond the pen base housing, and the dial knob assembly is shifted proximally and farther away from the housing. Drive sleeve 710 is held in rotatably fixed fashion by the engagement of lugs 655 within the housing splines. If the user rotates beyond a desired dose, the dose knob assembly and dial 680, and therefore the barrel 700, may be rotated in the opposite direction, which operation spins the dial 680 back down the drive sleeve 710. During this dialing down, the drive sleeve is held in rotatably fixed fashion due to its resistance to rotation attributable to lugs 655. During the rotation of barrel 700, which is axially stationary relative to the drive sleeve, display 871 displays a continuously changing value of the amount of medication that pen 620 would inject if operated via plunging at any given point during that rotation. In particular, display 871 is controlled by microprocessor 867, which recognizes the rotational position of barrel 700 relative to drive sleeve 710 based on input from the workings of the matrix pattern 802, rings 820-825, slider assembly 838, and circuit board 865. The user halts the dial rotation when she observes that display 871 indicates the quantity of medication desired to be injected. At this point, injection pen 620 is configured as shown in the cross-sectional view of FIG. 25, as the cap assembly and cover 658 have previously been taken off during the priming step as is conventional.

The user is now prepared to inject the set dose, which injecting operation is performed in two phases. Initially, and in the first phase, the pen is mechanically transitioned from a dosing mode to an injecting mode by proximally shifting the dose knob and dial a small distance, such as 0.080 inches of travel back into the pen housing. In particular, the user, typically with her thumb, applies a plunging force on the proximal face of dial knob cover 695. This plunging places an axial load on dial threads 685, which loading, via the drive sleeve thread 712, advances drive sleeve assembly 708 distally within pen 620 and without rotation of dial 680 relative to drive sleeve assembly due to frictional forces. This drive sleeve motion moves barrel 700 distally or forward due to the direct contact of the distal face of flange 716 with barrel lip 705. Distal travel of dial 680, drive sleeve 710, and barrel 700 is halted when barrel 700 reaches a location at which splines 704 mate with the housing bulkhead splines, at which time the barrel is rotatably fixed, and the dial, being rotatably keyed to the barrel, is also rotatably fixed.

Figure 26:
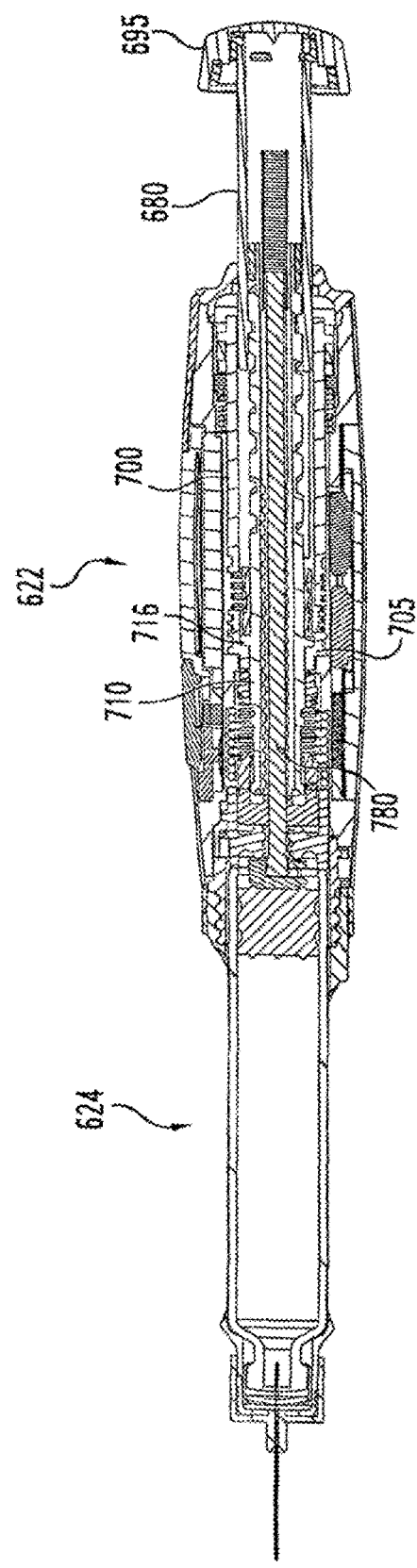
FIG. 26 is a cross-sectional view conceptually similar to the view of FIG. 25 after the dose setting knob has been slightly plunged so as to mechanically transition the pen to a dose injecting state.
Figure 27:
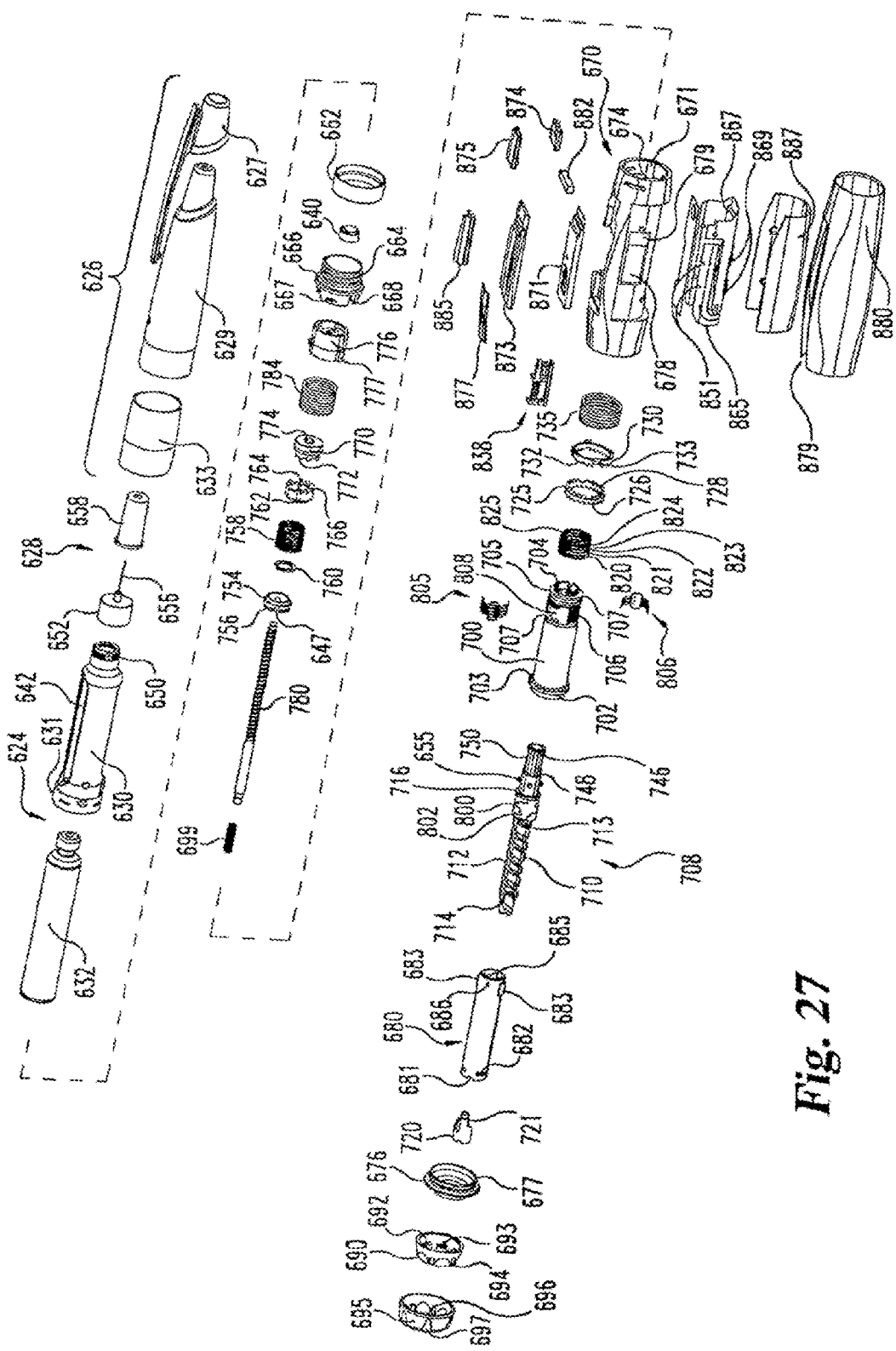
FIG. 27 is an exploded rear perspective view of the injection pen of FIG. 23.

When pen 620 has reached this state, which is shown in FIG. 26, the second phase of the injecting operation begins, as any further plunging force applied to the dial knob translates the dial knob assembly and dial 680 distally and without rotation, which translation produces rotation of drive sleeve 710. As drive sleeve 710 is rotated, the injection clutch 762 is also caused to rotate, which forces the rotation of the injection screw 780, which due to its engagement with the injection nut, advances the screw within the cartridge to force medicine out of the needle. As drive sleeve 710 rotates, the injection clicker 754 bounces in and out of the housing splines to produce injection clicks. The dial 680 is plunged until it reaches a plunged axial position corresponding to the position shown in FIG. 24, at which position dial thread 685 abuts zero stop 713 and rotation of drive sleeve 708 is halted. During this second phase, if the injection nut 776 has floated backward at all, the injection nut spring 784 finishes the injection by moving nut 776 distally when plunging of the dial is complete.

During both phases of the injecting operation, microcontroller 867 continuously receives the input from the electronic sensors that pick up relative rotational motion of the barrel 700 and the drive sleeve assembly 708. Display 871, throughout the entire injection process, displays the quantity still to be injected in real time, subject to the limitations of the electronics, which may allow the display to be updated only, for example, eight times per second. Because the injection switch 853 is activated when the barrel is moved distally, the microprocessor uses input from switch 853 to distinguish between dialing a dose and injection. The switch signal also may be used by the microprocessor to cause the time, date and amount being injected to be stored in memory for later reference.

After injection pen 620 is used to inject the set dose, controller 867 automatically returns to an off state, and the display elements of display 871 all turn off, following a certain time period of inactivity. In the event after dose setting no injection is immediately made, the display remains on until the injection is made, after which the pen turns off after the above-described inactivity. As the process of fully plunging the dose setting knob assembly and dial 680 during pen use automatically resets them, setting the dose the next time pen 620 is used simply requires rotating the dial knob assembly and dial 680 from their plunged position and without further manipulation.

Microcontroller 867 can use input received from injection switch 853 and the electronic sensors that pick up relative rotational motion of the barrel and the drive sleeve assembly to diagnose whether the injection pen is operating properly. For example, the pen can be programmed to display an error if the microcontroller senses the injection switch 853 is activated while the electronic sensors are indicating that the dose is being dialed up. In addition, an error message can also be communicated to the user via the display if the microcontroller senses that the injection switch 853 has not been activated, yet the input from the electronic sensors suggest that the dial sensing is of dubious accuracy, such as caused by the dial being manually rotated too rapidly by the user.

While one particular mechanism for converting rotation of the drive sleeve into an axial motion of the cartridge piston is disclosed in FIGS. 23-27, other less complicated mechanisms known in the art, such as one in which the drive sleeve is directly threaded with a drive screw, can be substituted within the scope of the present invention.

While this invention has been shown and described as having multiple designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

We claim:

1. A doseable quantity identifier for a medication injector apparatus having a dose setting mechanism operable to select a volume of medicine to be delivered from a held cartridge, comprising:
   a rotational matrix disposed on a first component of the apparatus;
   a sensor for electrically sensing the rotational matrix, said sensor disposed on a second component of the apparatus which experiences rotational motion relative to the first component during operation of the dose setting mechanism;
   whereby data of said rotational matrix sensible by said sensor is thereby indicative of an arrangement of the dose setting mechanism;
   a controller circuited with said sensor which interprets data of said rotational matrix sensed by said sensor to determine a quantity of medicine to be delivered from the cartridge during injection; and
   a visible display that displays the quantity of medicine to be delivered as determined by said controller;
   wherein said rotational matrix includes a plurality of rows and a plurality of columns, wherein said sensor includes a plurality of electrical contacts, each of said contacts aligned with a different row of said rotational matrix, wherein said data of said rotational matrix is in the form of the presence or absence of an electrically conductive material at intersections of said rows and columns of said rotational matrix, and wherein said plurality of electrical contacts and said rotational matrix are cooperatively configured such that when the first and second components are relatively rotationally shifted from a first rotational position, a change in data of said rotational matrix sensed by any single electrical contact does not produce a pattern corresponding to a rotational position that is within a range of rotational positions in either direction away from the first rotational position, said range being inclusively between two and at least three positions.

2. The doseable quantity identifier of claim 1 wherein said at least three positions is six positions.

3. A doseable quantity identifier for a medication injector apparatus having a dose setting mechanism operable to select a volume of medicine to be delivered from a held cartridge, comprising:
   a rotational matrix disposed on a first component of the apparatus;
   a sensor for electrically sensing the rotational matrix, said sensor disposed on a second component of the apparatus which experiences rotational motion relative to the first component during operation of the dose setting mechanism;
   whereby data of said rotational matrix sensible by said sensor is thereby indicative of an arrangement of the dose setting mechanism;
   a controller circuited with said sensor which interprets data of said rotational matrix sensed by said sensor to determine a quantity of medicine to be delivered from the cartridge during injection; and
   a visible display that displays the quantity of medicine to be delivered as determined by said controller;
   wherein said rotational matrix includes a plurality of rows and a plurality of columns, wherein said sensor includes a plurality of electrical contacts, each of said contacts aligned with a different row of said rotational matrix, wherein said data of said rotational matrix is in the form of the presence or absence of an electrically conductive material at intersections of said rows and columns of said rotational matrix, and wherein said plurality of electrical contacts and said rotational matrix are cooperatively configured such that data of said rotational matrix of each column of said rotational matrix is not unique, and wherein said controller is adapted to identify the correct relative rotational positioning of the first and second components based upon a previous valid positioning thereof and a range of positions adjacent to said previous valid positioning on either side.

* * * * *